(12) United States Patent
Bardell et al.

(10) Patent No.: US 8,741,233 B2
(45) Date of Patent: Jun. 3, 2014

(54) DISPOSABLE CARTRIDGE FOR FLUID ANALYSIS

(75) Inventors: Ron Bardell, St. Louis Park, MN (US); Tzu-Yu Wang, Maple Grove, MN (US); Mark Washa, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 50 days.

(21) Appl. No.: 13/337,889

(22) Filed: Dec. 27, 2011

(65) Prior Publication Data

US 2013/0164773 A1    Jun. 27, 2013

(51) Int. Cl.
*G01N 21/00*    (2006.01)

(52) U.S. Cl.
USPC ........... 422/554; 422/502; 422/504; 422/537; 422/430; 422/73; 422/68.1; 422/63; 422/400

(58) Field of Classification Search
USPC ..................... 422/63, 68.1, 73, 400
See application file for complete search history.

(56) References Cited

U.S. PATENT DOCUMENTS

| | | | |
|---|---|---|---|
| 3,822,095 A | 7/1974 | Hirschfeld | |
| 3,928,094 A | 12/1975 | Angell | |
| 3,976,862 A | 8/1976 | Curbelo | |
| 4,284,412 A | 8/1981 | Hansen et al. | |
| 4,478,076 A | 10/1984 | Bohrer | |
| 4,478,077 A | 10/1984 | Boher | |
| 4,501,144 A | 2/1985 | Higashi et al. | |
| 4,599,000 A | 7/1986 | Yasuyoshi | |
| 4,651,564 A | 3/1987 | Johnson et al. | |
| 4,683,159 A | 7/1987 | Bohrer et al. | |
| 4,695,034 A | 9/1987 | Shimizu et al. | |
| 4,704,033 A | 11/1987 | Fay et al. | |
| 4,745,279 A | 5/1988 | Karkar et al. | |
| 4,818,263 A | 4/1989 | Mitch | |
| 4,874,949 A | 10/1989 | Harris et al. | |
| 4,911,616 A | 3/1990 | Laumann, Jr. | |
| 4,932,989 A | 6/1990 | Presby | |
| 4,980,292 A | 12/1990 | Elbert et al. | |
| 5,017,497 A | 5/1991 | de Grooth et al. | |
| 5,050,429 A | 9/1991 | Nishimoto et al. | |
| 5,078,581 A | 1/1992 | Blum et al. | |
| 5,082,242 A | 1/1992 | Bonne et al. | |
| 5,085,562 A | 2/1992 | van Lintel | |
| 5,096,388 A | 3/1992 | Weinberg | |

(Continued)

FOREIGN PATENT DOCUMENTS

| | | |
|---|---|---|
| DE | 10122321 | 4/2002 |
| EP | 0269076 | 6/1988 |

(Continued)

OTHER PUBLICATIONS

Card Design #48, disclosed on Jun. 19, 2009.

(Continued)

*Primary Examiner* — Sally Merkling
(74) *Attorney, Agent, or Firm* — Seager Tufte Wickhem LLC

(57) ABSTRACT

A disposable blood analysis cartridge for analyzing a blood sample including an optical light scattering measurement channel is described. In use, processed sample may be introduced into a sheath fluid channel at an angle, α, of approximately 90 degrees, relative to the direction of flow of the sheath fluid. In addition, delivering the sample from the side into the sheath fluid may facilitate better positioning of the core within the hydrodynamic focusing channel for measurement.

9 Claims, 11 Drawing Sheets

(56) References Cited

U.S. PATENT DOCUMENTS

| | | | |
|---|---|---|---|
| 5,108,623 | A | 4/1992 | Cangelosi et al. |
| 5,129,794 | A | 7/1992 | Beatty |
| 5,171,132 | A | 12/1992 | Miyazaki et al. |
| 5,176,358 | A | 1/1993 | Bonne et al. |
| 5,185,641 | A | 2/1993 | Igushi et al. |
| 5,194,909 | A | 3/1993 | Tycko |
| 5,219,278 | A | 6/1993 | van Lintel |
| 5,224,843 | A | 7/1993 | van Lintel |
| 5,244,537 | A | 9/1993 | Ohnstein |
| 5,323,999 | A | 6/1994 | Bonne et al. |
| 5,441,597 | A | 8/1995 | Bonne et al. |
| 5,452,878 | A | 9/1995 | Gravesen et al. |
| 5,457,526 | A | 10/1995 | Kosaka |
| 5,510,267 | A | 4/1996 | Marshall |
| 5,528,045 | A | 6/1996 | Hoffman et al. |
| 5,570,193 | A | 10/1996 | Landa et al. |
| 5,601,080 | A | 2/1997 | Oppenheimer |
| 5,616,501 | A | 4/1997 | Rodriguez |
| 5,633,724 | A | 5/1997 | King et al. |
| 5,683,159 | A | 11/1997 | Johnson |
| 5,716,852 | A | 2/1998 | Yager et al. |
| 5,717,631 | A | 2/1998 | Carley et al. |
| 5,726,751 | A | 3/1998 | Altendorf et al. |
| 5,757,476 | A | 5/1998 | Nakamoto et al. |
| 5,760,900 | A | 6/1998 | Ito et al. |
| 5,793,485 | A | 8/1998 | Gourley |
| 5,799,030 | A | 8/1998 | Brenner |
| 5,822,170 | A | 10/1998 | Cabuz et al. |
| 5,836,750 | A | 11/1998 | Cabuz |
| 5,837,547 | A | 11/1998 | Schwartz |
| 5,839,807 | A | 11/1998 | Perlo |
| 5,863,502 | A | 1/1999 | Southgate et al. |
| 5,880,474 | A | 3/1999 | Norton et al. |
| 5,893,722 | A | 4/1999 | Hibbs-Brenner et al. |
| 5,901,939 | A | 5/1999 | Cabuz et al. |
| 5,922,210 | A | 7/1999 | Brody et al. |
| 5,932,100 | A | 8/1999 | Yager et al. |
| 5,948,684 | A | 9/1999 | Weigl et al. |
| 5,970,315 | A | 10/1999 | Carley et al. |
| 5,971,158 | A | 10/1999 | Yager et al. |
| 5,972,710 | A | 10/1999 | Weigl et al. |
| 5,974,867 | A | 11/1999 | Forster et al. |
| 6,007,775 | A | 12/1999 | Yager |
| 6,032,689 | A | 3/2000 | Tsai et al. |
| 6,054,335 | A | 4/2000 | Sun et al. |
| 6,082,185 | A | 7/2000 | Saaski |
| 6,091,197 | A | 7/2000 | Sun et al. |
| 6,091,537 | A | 7/2000 | Sun et al. |
| 6,094,293 | A | 7/2000 | Yokoyama et al. |
| 6,097,485 | A | 8/2000 | Lievan |
| 6,097,859 | A | 8/2000 | Solgaard et al. |
| 6,106,245 | A | 8/2000 | Cabuz |
| 6,109,889 | A | 8/2000 | Zengerie et al. |
| 6,116,756 | A | 9/2000 | Peeters et al. |
| 6,124,663 | A | 9/2000 | Haake et al. |
| 6,139,800 | A | 10/2000 | Chandler |
| 6,179,586 | B1 | 1/2001 | Herb et al. |
| 6,184,607 | B1 | 2/2001 | Cabuz et al. |
| 6,215,221 | B1 | 4/2001 | Cabuz et al. |
| 6,237,619 | B1 | 5/2001 | Maillefer et al. |
| 6,240,944 | B1 | 6/2001 | Ohnstein et al. |
| 6,249,341 | B1 | 6/2001 | Basiji et al. |
| 6,281,975 | B1 | 8/2001 | Munk |
| 6,382,228 | B1 | 5/2002 | Cabuz et al. |
| 6,537,501 | B1 | 3/2003 | Holl et al. |
| 6,537,514 | B1 | 3/2003 | Holl et al. |
| 6,549,275 | B1 | 4/2003 | Cabuz et al. |
| 6,576,194 | B1 | 6/2003 | Holl et al. |
| 6,597,438 | B1 | 7/2003 | Cabuz et al. |
| 6,656,431 | B2 | 12/2003 | Holl et al. |
| 6,712,925 | B1 | 3/2004 | Holl et al. |
| 6,830,729 | B1 | 12/2004 | Holl et al. |
| 6,852,284 | B1 | 2/2005 | Holl et al. |
| 7,226,562 | B2 | 6/2007 | Holl et al. |
| 2003/0057968 | A1 | 3/2003 | Wang et al. |
| 2003/0142291 | A1 | 7/2003 | Padmanabhan et al. |
| 2004/0065143 | A1 | 4/2004 | Husher |
| 2004/0109386 | A1 | 6/2004 | Gold et al. |
| 2004/0154933 | A1 | 8/2004 | Cosofret |
| 2004/0233424 | A1 | 11/2004 | Lee et al. |
| 2005/0105077 | A1 | 5/2005 | Padmanabhan et al. |
| 2005/0255600 | A1 | 11/2005 | Padmanabhan et al. |
| 2006/0127275 | A1 | 6/2006 | Holl et al. |
| 2006/0263888 | A1 | 11/2006 | Fritz et al. |
| 2007/0009386 | A1 | 1/2007 | Padmanabhan et al. |
| 2007/0166196 | A1* | 7/2007 | Bardell et al. ............... 422/68.1 |

FOREIGN PATENT DOCUMENTS

| | | |
|---|---|---|
| EP | 0694784 | 1/1996 |
| EP | 1001326 | 5/1999 |
| EP | 1134548 | 9/2001 |
| EP | 1359419 | 5/2003 |
| JP | 60082865 | 12/1983 |
| JP | 61066947 | 4/1986 |
| JP | 10073528 | 3/1998 |
| JP | 2000056228 | 2/2000 |
| JP | 2004257756 | 9/2004 |
| WO | WO 9527199 | 10/1995 |
| WO | WO 9960397 | 11/1999 |
| WO | WO 0109598 | 2/2001 |
| WO | WO 0210713 | 2/2002 |
| WO | WO 0210714 | 2/2002 |
| WO | WO 2004059316 | 7/2004 |
| WO | WO 2005090983 | 9/2005 |
| WO | WO 2005108963 | 11/2005 |
| WO | WO 2005114142 | 12/2005 |
| WO | WO 2005114144 | 12/2005 |
| WO | WO 2007/076549 | 7/2007 |
| WO | WO 2007/084232 | 7/2007 |
| WO | WO 2010/005467 | 1/2010 |
| WO | WO 2011/075667 | 6/2011 |

OTHER PUBLICATIONS

U.S. Appl. No. 13/337,916, filed Dec. 27, 2011.
U.S. Appl. No. 13/337,911, filed Dec. 27, 2011.
U.S. Appl. No. 13/337,900, filed Dec. 27, 2011.
Altendorf et al, "Results Obtained Using a Prototype Microfluidics-Based Hematology Analyzer", SPIE Biomedical Optics 97, 1997.
Altendorf et al., "Differential Blood Cell Counts Obtained Using a MicroChannel Based Flow Cytometer", Solid State Sensors & Actuators, vol. 1, 531, 1997.
Altendorf et al., "Implementation of Novel Optical Detection Methods for Clinically Important Blood Analytes Using Microfabricated Flow Structures (T-Sensors™)", MicroTAS 98, Banff, Canada, Apr. 1998.
Altendorf et al., "Microfabrication Technology for Research and Diagnostics, Silicon MicroChannel Optical Flow Cytometry", SPIE Proceedings, Biomedical Optics 96, Jan. 1996.
Cabuz et al., "Mesoscopic Sampler Based on 3D Array of Electro-statically Activated Diaphragms", The 10th Int. Conf. On Solid-State Sensors and Actuators, Transducers'99, Jun. 7-12, 1999, Sendai Japan, p. 1890-1891.
Darling et al., "Integration of Microelectrodes With Etched Microchannels for In-Stream Electrochemical Analysis", MicroTAS 98, Banff, Canada, Apr. 1998.
Fedderetal., "Laminated High-Aspect-Ratio Microstructures in a Conventional CMOS Process", Proc. Micro Electro Mechanical Systems Workshop, MEMS 96, San Diego, California, Feb. 11-15, 1996, pp. 13-18.
Hatch et al., "Microfluidic Approaches to Immunoassays", SPIE conference on Micromachining and Microfabrication Symposium at Santa Clara, CA, Sep. 20-22, 1999.
HemoCue Hb201+, Operating Manual, pp. 1-41, prior to Dec. 2006.
http://www.micronics.net/hfilter.htm, pp. 1-3, downloaded Jun. 14, 2000.
http://www.micronics.net/mcytometry.htm, pp. 1-4, downloaded Jun. 14, 2000.
http://www.micronics.net/orcafluidics.htm, pp. 1-4, downloaded Jun. 14, 2000.

(56) References Cited

OTHER PUBLICATIONS http://www.micronics.net/tsensor.htm, pp. 1-4, downloaded Jun. 14, 2000.

Huang et al., "Development of a Flow Cytometry Based Miniature Chemical Fluid Analysis System Using Fluorescent Microbeads", SPIE Biomedical Optics, BIOS 97, conference proceedings, 1997.

Lamvik et al., Nonlabeled Secondary Antibodies Augment/Maintain the Binding of Primary, Specific Antibodies to Cell Membrande Antigens, Cytometery 45, pp. 187-193, 2001.

Lehman et al., "High-Frequency Modulation Characteristics of Red VCSELs", Electronics Letters, Feb. 13, 1997, vol. 33(4), pp. 298-300. Copyright 1997 IEEE.

Ohnstein etal., "Micromachined Silicon Microvalve", Proceedings of MEMS, 1990, IEEE Micro Electromechanical Systems, Napa Valley, California, Feb. 11-14, 1990, pp. 95-98.

Roulet et al., "Fabrication of Multilayer Systems Combining Microfluidic and Microoptical Elements for Fluorescence Detection," Journal of Microelectromechanical Systems, vol. 10 No. 44, pp. 483-491, Dec. 4, 2001.

Shapiro, "Practical Flow Cytometry", third edition, 1995, p. 237.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen et al., "Four-Parameter White Blood Cell Differential Counting Based on Light Scattering Measurements", Alan R. Liss, Inc., Cytometery 9:39-43, 1988.

Toshiyoshi et al., "Micromechanical Lens Scanner for Fiber Optic Switches", Proc. 3rd International Conference on Micro Opto Electro Mechanical Systems (MOEMS 99), Aug. 30-Sep. 1, 1999, Mainz, Germany, pp. 165-170.

Toshiyoshi et al., "Surface Micromachined 2D Lens Scanner Array", Proc. IEEE7LEOS International Coference on Optical EMMS/Sheraton Kauai Resort, Kauai, Hawaii, Aug. 21-24, 2000, 3 pages.

Tuantranont et al., "Flip Chip Integration of Lenslet Arrays on Segmented Deformable Micromirrors", Part of the Symposium on Design, Test and Microfabrication of MEMS and MOEMS, Paris, France, Mar.-Apr. 1999, SPIE vol. 3680, 0277-786X/99, pp. 668-678.

Tuantranont et al., "MEMS-Controllable Microlens Array for Beam Steering and Precision Alignment in Optical Interconnect Systems", Solid-State Sensor and Actuator Workshop, Hilton Head Island, South Carolina, Jun. 4-8, 2000, pp. 101-104.

Weigl et al, "Optical and Electrochemical Diffusion-Based Detection of Analytes in Complex Samples Using Microfabricated Flow Structures (T-SensorSTM)", Micro- and nanofabn'cated electro-optical mechanical systems for biomedical and environmental applications II—SPIE vol. 3606, Jan. 25-26, 1999.

Weigl et al, "Silicon-Microfabricated Diffusion-Based Optical Chemical Sensor", Reprint from "Sensors & Actuators" B 38-39,452-457, 1997.

Weigl et al, "Simultaneous Self-Referencing Analyte Determination in Complex Sample Solutions Using Microfabricated Flow Structures (T-Sensors™)", Proceedings of MicroTAS 98, 81-4, Banff, Canada, 1998.

Weigl et al., "Diffusion-Based Optical Chemical Detection in Silicon Flow Structures", Analytical Methods & Instrumentation, uTTAS 96 special edition, 1996.

Weigl et al., "Fluorescence and Absorbance Analyte Sensing in Whole Blood and Plasma Based on Diffusion Separation in Silicon-Microfabricated Flow Structures (T-Sensors™)", Biomedical Optics, vol. 6, No. 1, Jul. 1997.

Weigl et al., "Rapid Sequential Chemical Analysis Using Multiple Fluorescent Reporter Beads", uTTAS 96 Conference Proceedings, 1996.

Weigl etal, "Microfluidic Diffusion-Based Separation and Detection", Science, vol. 283, pp. 346-347, Jan. 15, 1999.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorSTm Technology", Medical Design Online, http://news.medicaldesignonline.com/featuresarticles/19990416-5922.html, Apr. 1999.

Yager et al., "Applying Microfluidic Chemical Analytical Systems to Imperfect Samples", Micro Total Analysis Systems 98, D. Harrison & A. van den Berg (ed.), Kluwer Academic Publishers, Dordrecht, 207-212, 1998.

Yager et al., "Design of Microfluidic Sample Preconditioning Systems for Detection of Biological Agents in Environmental Samples", Yager, M. etal., SPIE Proceedings, 3515, 252-259, 1998.

\* cited by examiner

DISPOSABLE CARTRIDGE FOR FLUID ANALYSIS

TECHNICAL FIELD

The present disclosure relates generally to disposable fluidic cartridges for analysis of a fluid, and more particularly to disposable fluidic cartridges for analysis of blood and/or other biological fluids.

BACKGROUND

Chemical and/or biological analysis is important for life sciences research, clinical diagnostics, and a wide range of environmental and process monitoring. In some cases, sample analyzers are used to perform and/or assist in performing chemical and/or biological analysis of a sample fluid. The sample fluid may be a liquid or a gas, depending on the application.

Many sample analyzers are rather large devices that are used in a laboratory environment by trained personnel. To use many sample analyzers, a collected sample must first be processed, such as by diluting the sample to a desired level, adding appropriate reagents, centrifuging the sample to provide a desired separation, and so on, prior to providing the prepared sample to the sample analyzer. To achieve an accurate result, such sample processing must typically be performed by trained personnel, which can increase the cost and time required to perform the sample analysis.

Many sample analyzers also require operator intervention during the analysis phase, such as requiring additional information input or additional processing of the sample. This can further increase the cost and time required to perform a desired sample analysis. Also, many sample analyzers merely provide raw analysis data as an output, and further calculations and/or interpretation must often be performed by trained personnel to make an appropriate clinical or other decision.

SUMMARY

The present disclosure relates generally to disposable fluidic cartridges for analysis of a fluid, and more particularly to disposable fluidic cartridges for analysis of blood and/or other biological fluids. In one illustrative embodiment, a disposable blood analysis cartridge for analyzing a blood sample may be provided. The disposable blood analysis cartridge may include: a sample loading channel for receiving a fluid sample; a reagent channel in fluid communication with the sample loading channel, the reagent channel including a mixing region wherein the fluid sample is mixed with a reagent to produce a processed sample; a sheath channel in fluid communication with the reagent channel, the sheath channel for carrying a flow of sheath fluid, wherein the reagent channel is configured to deliver the processed sample through a sidewall of the sheath channel and at an angle greater than 5 degrees relative to a direction of fluid flow of the sheath fluid within the sheath channel. In some cases, the reagent channel may be configured to deliver the processed sample through a sidewall of the sheath channel and at an angle of approximately 90 degrees relative to a direction of fluid flow of the sheath fluid within the sheath channel In another example, a disposable blood analysis cartridge may include a sample introduction port for receiving a fluid sample; a sample loading channel in fluid communication with the sample introduction port; a reagent channel in fluid communication with the sample loading channel, the reagent channel including a mixing region wherein the fluid sample is mixed with a reagent to produce a processed sample; a sheath channel in fluid communication with the reagent channel, the sheath channel for carrying a flow of sheath fluid, wherein the reagent channel is configured to deliver the processed sample through a sidewall of the sheath channel and at an angle relative to a direction of fluid flow of the sheath fluid within the sheath channel; a measurement channel including a hydrodynamic focusing region disposed adjacent a transparent window, wherein the processed sample is carried by the sheath fluid from the sheath channel into the measurement channel and past the transparent window; and an on-board waste storage reservoir in fluid communication with the measurement channel, the on-board waste storage reservoir configured to receive the processed sample and the sheath fluid after they have passed through the measurement channel.

An illustrative method of analyzing a blood sample in a cartridge may include receiving a blood sample in the cartridge. The cartridge may include a microfluidics circuit that includes a reagent channel in fluid communication with a sheath channel and an optical light scattering measurement channel including a hydrodynamic focusing region. A sheath fluid may be introduced into the sheath channel. At least a portion of the blood sample may be delivered into the sheath channel at an angle of between about 25 and 115 degrees relative to a direction of the fluid flow within the sheath channel, wherein the sheath fluid carries the portion of the blood sample into the optical light scattering measurement channel. A measurement of an optical light scattering property of the blood sample may then be taken.

The preceding summary is provided to facilitate an understanding of some of the innovative features unique to the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following detailed description of various embodiments in connection with the accompanying drawings, in which.

Figure 1:
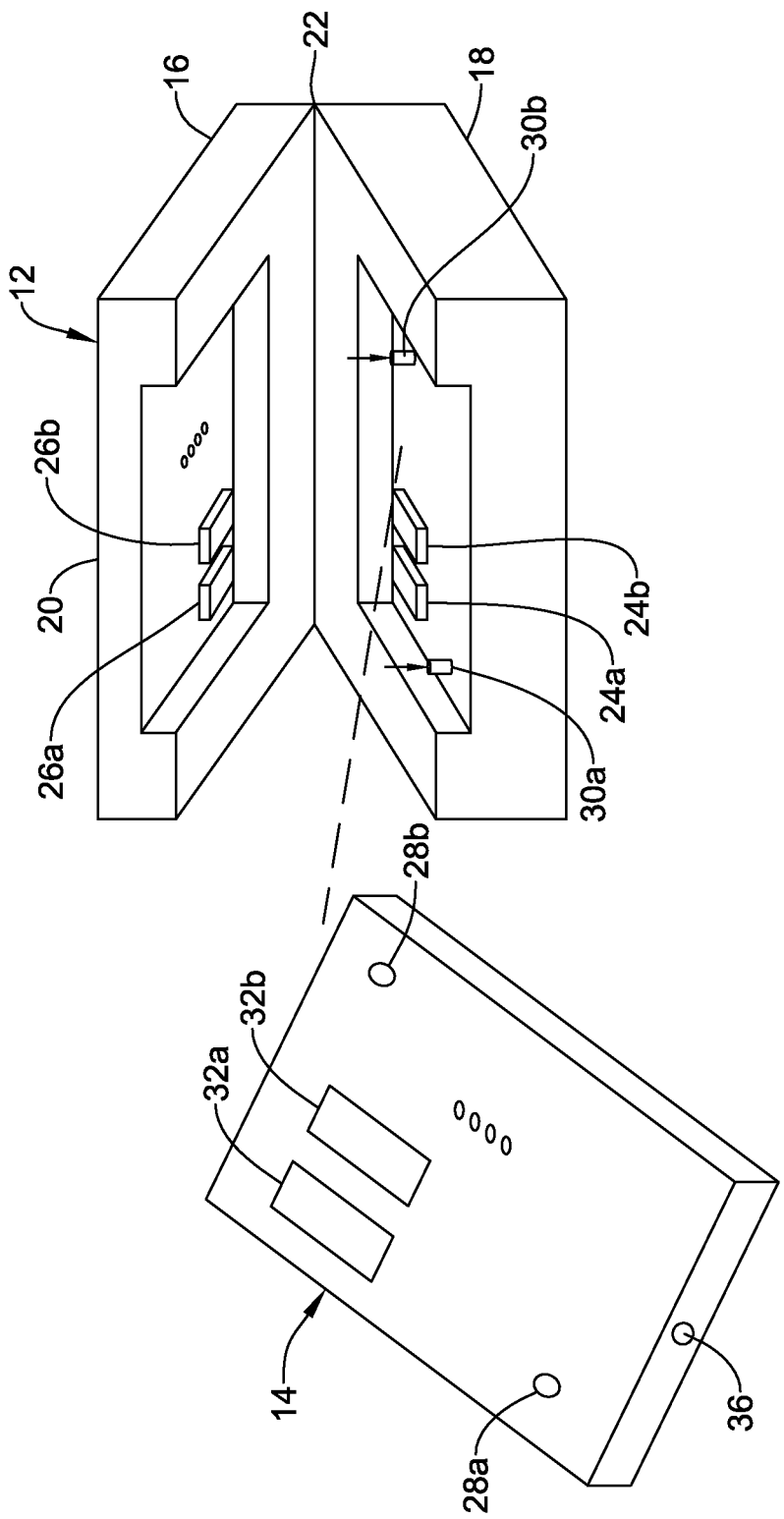
FIG. 1 is a perspective view of an illustrative sample analyzer and cartridge.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings wherein like reference numerals indicate like elements throughout the several views. The detailed description and drawings show several embodiments which are meant to illustrative of the claimed disclosure.

The present disclosure relates generally to disposable fluidic cartridges for analysis of a fluid and more particularly, to disposable fluidic cartridges for analysis of a variety of biological fluids including, but not limited to, blood, blood products (e.g. controls, linears, calibrators, etc.), urine, and/or other biological fluids from mammalian and non-mammalians sources. In some cases, the present disclosure may provide sample analyzers that are simple to operate and have a reduced risk of providing erroneous results. In some examples, the sample analyzer may be, for example, a blood analyzer such as a flow cytometer, a hematology analyzer, a clinical chemistry analyzer (e.g., glucose analyzer, ion analyzer, electrolytes analyzer, dissolved gasses analyzer, and so forth), a urine analyzer or any other suitable analyzer, as desired.

FIG. 1 is a perspective view of an illustrative sample analyzer 12 and analysis cartridge 14. In some cases, the sample analyzer 12 is adapted to be used at the point of care of a patient, such as in a doctor's office, in the home, or elsewhere in the field. The ability to provide a sample analyzer 12 that can be reliably used outside of the laboratory environment, with little or no specialized training, may help streamline the sample analysis process, reduce the cost and burden on medical personnel, and increase the convenience of sample analysis for many patients, including those that require relatively frequent blood monitoring/analysis. While the sample analyzer 12, as depicted in the illustrative example provide in FIG. 1, may include a flow cytometer, it will be understood that the sample analyzer 12 may include any suitable type of sample analyzer, as desired.

In the illustrative example of FIG. 1, sample analyzer 12 may include a housing 16 having a base 18, a cover 20, and a hinge 22 that attaches the base 18 to the cover 20. Depending on the types of analyses being performed, the base 18 may include one or more light sources. For example, in some embodiments, the base 18 may include a first light source 24a for optical light scattering measurements and a second light source 24b for optical absorption measurements. In some case, depending upon the application, the base 18 may include additional light sources for additional measurements. In addition, the base 18 may include associated optics and the necessary electronics for operation of the sample analyzer including the light sources 24a and 24b. Each of the light sources 24a and 24b may be a single light source or a multiple light source, depending on the application. The illustrative cover 20 may include a pressure source (e.g., pressure-chambers with control microvalves) and one or more light detectors for detecting light emitted from the one or more light sources. In some cases, the cover 20 may include a first light detector 26a and a second light detector 26b, each with associated optics and electronics. Each of the light detectors 26a and 26b may also be a single light detector or multiple light detectors, depending on the application. Polarizers and/or filters may also be provided, if desired, depending on the application.

It is contemplated that the disposable blood analysis cartridge 14 may include a microfluidic circuit. The microfluidic circuit may be suitable for processing (e.g. lyse, sphere, dilute, mix, etc.) a sample, and deliver the sample to an appropriate region of the cartridge 14 for analysis. In some embodiments, the microfluidic circuit may include an optical scattering measurement channel, an optical absorbance measurement channel, or both.

In some cases, the cartridge 14 may be formed from a laminated structure having multiple layers, with some layers including one or more channels passing through the layer. However, it is contemplated that the removable cartridge 14 may be constructed in any suitable manner including by injection molding, or any other suitable manufacturing process or approach, as desired.

In some cases, the disposable cartridge 14 may include holes 28a and 28b for receiving registration pins 30a and 30b in the base 18. This may help provide alignment and coupling between the different parts of the instrument, if desired. The removable cartridge 14 may also include a first transparent window 32a and a second transparent window 32b, which are in alignment with the first and second light sources 24a and 24b and the first and second detectors 26a and 26b, respectively. The cartridge 14 may also include a sample introduction port 36 for introduction of a fluid sample such as, for example, a whole blood sample into the cartridge 14. The whole blood sample may be obtained via a finger stick or a blood draw.

During use, and after a fluid sample has been delivered into the disposable cartridge 14 via the sample introduction port 36, the disposable cartridge 14 may be inserted into the housing 16. In some cases, the removable cartridge 14 may be inserted into the housing 16 when the cover 20 is in the open position. However, in other examples, the removable cartridge 14 may be inserted into the housing in any suitable way. For example, the housing may have a slot, and the disposable cartridge 14 may be inserted into the slot of the housing 16.

When the cover 20 is closed, the system may be pressurized. Once pressurized, the sample analyzer 12 may perform a blood analysis on the collected blood sample. In some cases, the blood analysis may include a complete blood count (CBC) analysis, but other types of analysis can be performed, depending on the application. In some cases, for example, the blood analysis may include, a red blood cell count (RBC), a platelet count (Plt), a mean cell hemoglobin concentration (MCHC), a mean cell volume (MCV), a relative distribution width (RDW), hemocrit (Hct) and/or a hemoglobin concentration (Hb). In some cases, the blood analysis on the collected blood sample may also a white blood cell count (WBC), three or five part white cell differentiation, total white blood cell count and/or on-axis white blood cell volume. After analysis is complete, the cartridge 14 may be disposed of in an appropriate waste receptacle.

Figure 2:
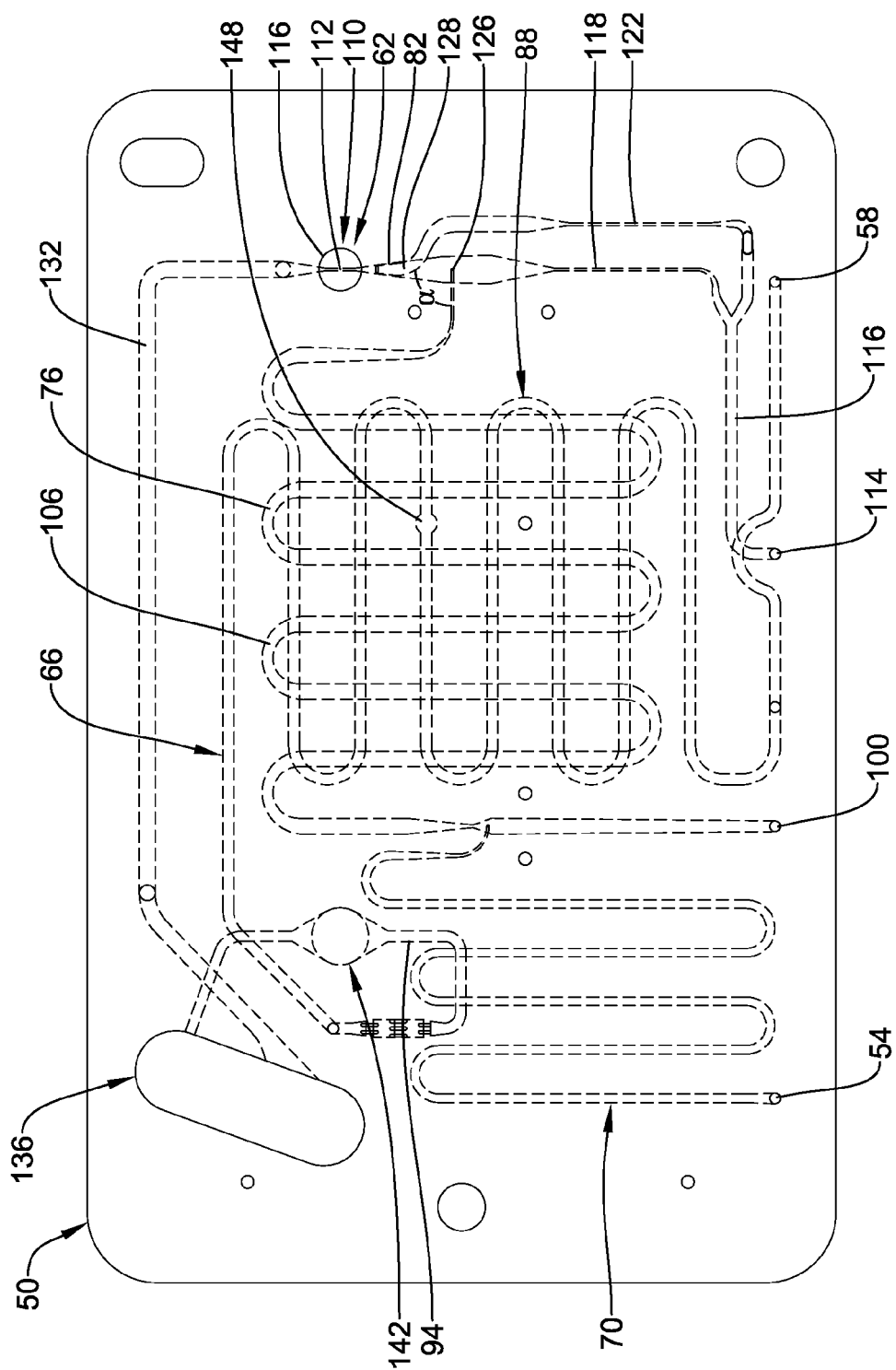
FIG. 2 is a front schematic view of an illustrative fluid analysis cartridge that may be received by a sample analyzer, such as the sample analyzer of FIG. 1.

FIG. 2 is a front schematic view of an illustrative fluid analysis cartridge 50 that may be received by a sample analyzer, such as the sample analyzer 12 discussed above. In some cases, the blood analysis cartridge 50 may be a disposable blood analysis cartridge. The cartridge 50 may be configured such that once a blood sample is received in the cartridge 50; the cartridge 50 may be self-contained such that special handling measures are not required. However, as with many biological samples, it would be recommend that ordinary precautionary measures be taken if desired.

In some cases, and as shown in the illustrative example of FIG. 2, the cartridge 50 may be configured for both optical light scattering measurements and optical absorbance measurements, and may be configured such that a pusher fluid, one or more reagents, and a sheath fluid, which may be necessary to move the sample through the different regions of the cartridge and process the sample for analysis, may be delivered by the sample analyzer 12.

In some cases, and as shown in FIG. 2, the cartridge 50 may include at least one sample introduction port 54 for introduction of a sample into the cartridge 50. In some cases, the cartridge 50 may also include a second sample introduction port 58, but this is not required. For example, in some cases, the cartridge 50 may include a single sample introduction port, coupled to a bifurcated sample delivery channel, wherein the bifurcated sample delivery channel is in fluid communication with two or more measurement regions of the cartridge 50. In many cases, the first and second sample introduction ports 54 and 58 may include an anti-coagulant coating provided on an inner surface thereof to facilitate sample loading. In other cases, the first and second sample introduction ports 54 and 58 may include a hydrophilic coating which may facilitate loading of the sample via capillary action. However, this is not required. In some cases, the sample introduction port may be configured to mate with and/or receive a syringe for delivery of a fluid sample into the cartridge 50, but again, this is not required. Any suitable fluid connection may be used.

As illustrated in the example shown in FIG. 2, the first sample introduction port 54 may be in fluid communication with a first measurement region 62 of the cartridge 50, and the second sample port 58 may be in fluid communication with a second measurement region 66 of the cartridge 50. In some cases, the first measurement region 62 is an optical light scattering measurement region 62 that may include a first sample loading channel 70, a reagent channel 76, and an optical light scattering measurement channel 82. In addition, the second measurement region 66 may be an optical absorbance measurement region 66, and may include a second sample loading channel 88 and an optical absorbance measurement channel 94.

Once a sample is loaded into the first sample loading channel 70, a pusher fluid may be introduced via the first sample introduction port 54 to push the sample from the first sample loading channel 70 into the reagent channel 76 which is in fluid communication with the first sample loading channel 70. In some cases, the reagent channel 76 may include a reagent introduction port 100 for introduction of one or more reagents into the reagent channel 76 for processing the sample. The number and/or type of reagents to be introduced into the reagent channel 76 may depend upon the application. For example, the reagents may include a lysing reagent, a sphering reagent, a diluent, etc. The reagent introduced through the reagent introduction port 100 may contact and mix with the sample entering the reagent channel 76 from the first sample loading channel 70. In some embodiments, the reagent channel 76 may include a number of bends or turns 106 that may increase the length of the reagent channel 76, which may increase the length of time the sample spends in the reagent channel. In some cases, as shown, the bend or turn 106 may be a substantially U-shaped bend or turn 106, and may help keep particles such as blood cells dispersed as the sample travels through the reagent channel 76. The increase in dwell or residence time may provide a sufficient amount of time needed for the reagent to properly react with and process the sample for analysis. The processed sample may then delivered from the reagent channel 76 to the optical light scattering measurement channel 82 for analysis using an optical light scattering measurement technique such as, for example, flow cytometry.

The optical scattering measurement channel 82 may include a hydrodynamic focusing region 110 having a narrow channel region 112 over which a transparent window 116 may be disposed. In some cases, the processed sample may be delivered from the reagent channel 76 to the optical measurement channel 82 at a location upstream relative to the hydrodynamic focusing region 110. In the example shown, sheath fluid may be introduced into the cartridge via a sheath fluid introduction port 114. The sheath fluid may be provided at such a flow rate that it surrounds the processed sample and forms a "sheath" around the sample "core". In some cases, the sheath fluid flow rate may be controlled such that it is higher than the processed sample flow rate to aid in core formation downstream within the hydrodynamic focusing region 110.

In some cases, as shown in the example shown in FIG. 2, the sheath fluid introduction port 114 may be fluidly coupled to a bifurcated sheath fluid delivery channel 116 including a first elongated sheath fluid sub channel 118 and a second elongated sheath fluid sub channel 122, but this is not required. The processed sample may be introduced into the first elongated sheath fluid channel 118 from the side at an intersecting region 126. In some cases, as shown, the processed sample may be introduced into first elongated sheath fluid sub channel at an angle, α, of approximately 90 degrees, relative to the direction of flow of the sheath fluid. It is contemplated that the processed sample may be introduced into first elongated sheath fluid sub channel at an angle, α, of between 5 and 175 degrees, between 25 and 115 degrees, between 45 and 135 degrees, between 60 and 150 degrees, between 85 and 95 degrees, or any other suitable angle relative to the direction of flow of the sheath fluid. This can be the case where only a single sheath fluid delivery channel is provided (not shown in FIG. 2), or a bifurcated sheath fluid delivery channel 116 is provided (as shown in FIG. 2).

When provided, the second elongated sheath fluid sub channel 122 may intersect with the first elongated sheath fluid sub channel 118 at a second intersection region 128, located downstream from the first intersection region 126. In some cases, and as shown in FIG. 2, the second elongated sheath fluid sub channel 122 may deliver a portion of the sheath fluid from a position located above the first sheath fluid sub channel 118 such that the sheath fluid from the second sheath fluid sub channel 122 enters the first sheath fluid sub channel 118 from the top. In some cases, the second elongated sheath fluid sub channel 122 may deliver another portion of the sheath fluid from a position located below the first sheath fluid sub channel 118 such that the sheath fluid from the second sheath fluid sub channel 122 enters the first sheath fluid sub channel 118 from the bottom. The combination of the processed sample entering the first sheath fluid sub channel 118 from the side coupled with the delivery of a portion of the sheath fluid from an upper position and/or a lower position may facilitate better positioning of the core within the hydrodynamic focusing region 110. In some cases, this configuration may provide three-dimensional hydrodynamic focusing of the processed sample within the sheath fluid flow, which may result in a more reliable and accurate measurement of sample properties in the optical light scattering measurement channel 82. In the example shown, the sheath fluid carries the processed sample into the hydrodynamic focusing region 110 for hydrodynamic focusing of the processed sample and analysis by flow cytometry. The processed sample then passes from the optical scattering measurement channel 82 into a waste channel 132 where it is carried to a waste storage reservoir 136. In some cases, the waste storage reservoir 136 may be a self-contained, on-card waste storage reservoir.

In some cases, and as discussed above, the cartridge 50 may include an optical absorbance measurement region 66. In some cases, as shown, at least a portion of the optical absorbance measurement region 66, such as the optical absorbance measurement channel 94, may pass over and/or under the optical light scattering measurement region 62 including the optical scattering measurement channel 82. For example, as shown in FIG. 2, the second sample loading channel 88 of the optical absorbance measurement region 66 passes over or under the reagent channel 76 of the optical light scattering measurement region 62.

In the example shown, sample may be introduced into the second sample loading channel 88 via a second sample introduction portion 58. In some cases, the sample may be a whole blood sample, but this is not required. Sample may flow from the second sample loading channel 88 into the optical absorbance measurement channel 94. The optical absorbance measurement channel 94 includes a cuvette 142 through which light may be passed to obtain an optical absorbance measurement which may be used to determine one or more of the sample properties. Sample may be delivered from the second sample loading channel 88 to the optical measurement channel 94 until the cuvette 142 is substantially filled with sample. In some cases, the second sample loading channel 88 may include an indicator window 148 which may serve as a visual reference point for sample loading. For example, sample loading may be ceased when sample is visible within the indicator window 148, indicating that the optical measurement channel 94 including the cuvette 142 has been substantially filled with sample and no further sample is needed.

In some embodiments, as shown, each of the optical light scattering measurement channel 82 and the optical absorbance measurement region 66 may be configured to deliver waste sample to a waste storage reservoir 136. In some embodiments, the waste storage reservoir 136 may be configured to be aspirated by the sample analyzer such as, for example, sample analyzer 12, but this not required. In other embodiments, the waste storage reservoir 136 may be configured such that it receives and collects the waste sample and contains the sample within the cartridge 50 such that the cartridge 50 containing the waste sample and any remaining unused sample and/or reagents can be disposed of after use.

Figure 3:
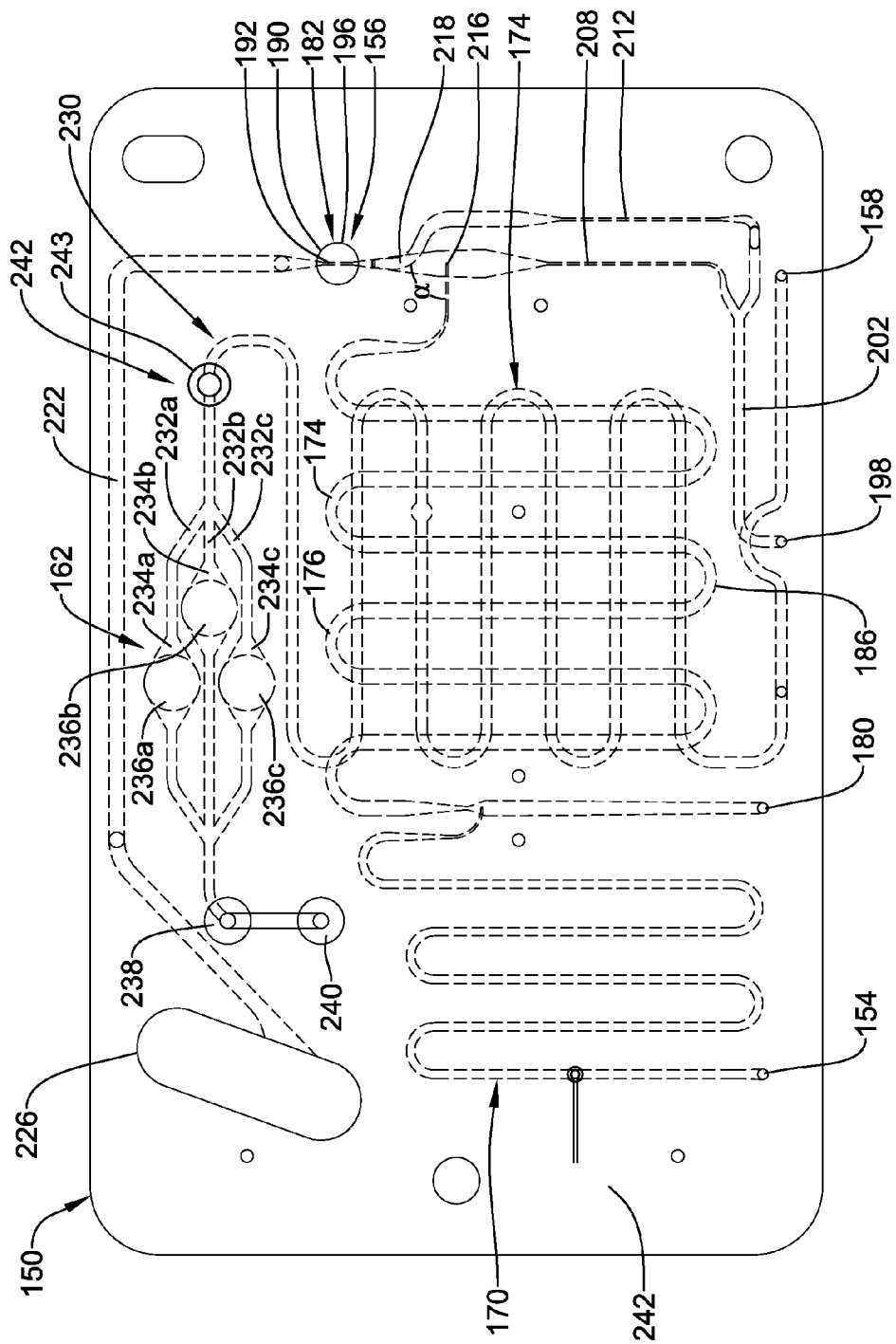
FIG. 3 is a front schematic view of an illustrative fluid analysis cartridge that may be received by a sample analyzer, such as the sample analyzer of FIG. 1.

FIG. 3 is a front schematic view of an illustrative fluid analysis cartridge 150 that may be received by a sample analyzer, such as the sample analyzer 12 of FIG. 1. In some cases, the blood analysis cartridge 150 is a disposable blood analysis cartridge. The cartridge 150 may be configured such that once a blood sample is received in the cartridge 150; the cartridge 150 becomes self-contained such that special handling measures are not required. However, as with many biological samples, it would be recommend that ordinary precautionary measures be taken if desired.

In some cases, as shown in the illustrative example of FIG. 3, the cartridge 150 may be configured for both optical light scattering measurements and optical absorbance measurements, and may be configured such that the necessary pusher fluid, one or more reagents, and a sheath fluid, which may be necessary to move the sample through the different regions of the cartridge and process the sample for analysis are delivered by the sample analyzer 12. As shown in the illustrative example provided by FIG. 3, cartridge 150 may include an optical light scattering measurement region 156 and an optical absorbance measurement region 162.

In some cases, as shown, the cartridge 150 may include at least one sample introduction port 154 for introduction of a sample into the cartridge 150. Additionally, the cartridge 150 may include a second sample introduction port 158, but this is not required. For example, in some cases, the cartridge 150 may include a single sample introduction port coupled to a bifurcated sample delivery channel, wherein the bifurcated sample delivery channel is in fluid communication with two or more measurement regions (e.g. the optical light scattering measurement region 156 and optical absorbance measurement region 162) of the cartridge 150. In many cases, the first and second sample introduction ports 154 and 158 may include an anti-coagulant coating provided on an inner surface thereof to facilitate sample loading. In other cases, the first and second sample introduction ports 154 and 158 may include a hydrophilic coating which may facilitate loading of the sample via capillary action. However, this is not required.

As illustrated in the example shown in FIG. 3, the first sample introduction port 154 may be in fluid communication with the optical light scattering measurement region 156 via a first sample loading channel 170. In addition, the second sample introduction port 158 may be in fluid communication with the optical absorbance measurement region 162 via second sample loading channel 174. Once sample is loaded into the first sample loading channel 170, a pusher fluid may be introduced via the first sample introduction port 154 to push the sample from the sample loading channel into a reagent channel 176, which is in fluid communication with the first sample loading channel 170. In some cases, the reagent channel 176 may include a reagent introduction port 180 for introduction of one or more reagents into the reagent channel 176 for processing the sample. The number and/or type of reagents to be introduced into the reagent channel may depend upon the application. For example, the reagents may include a lysing reagent, a sphering reagent, a diluent, etc. The reagent introduced through the reagent introduction port 180 may contact and mix with the sample entering the reagent channel 176 from the first sample loading channel 170. In some embodiments, the reagent channel 176 may include a number of bends or turns 186 that increase the length of the reagent channel 176, which may increase the length of time the sample spends in the reagent channel (sometimes referred to as dwell time). In some cases, as shown, the bend or turn 186 may be a substantially U-shaped bend or turn 186, but this is not required. The increase in dwell or residence time may provide a sufficient amount of time needed for the reagent to properly react with and process the sample for analysis. The processed sample may be delivered from the reagent channel 176 to the optical light scattering measurement region 156 for analysis using an optical light scattering measurement technique such as, for example, flow cytometry.

The optical scattering measurement region 156 may include an optical light scattering measurement channel 182 having a hydrodynamic focusing region 190 including a narrow channel region over which a light transparent window 196 may be disposed. In some cases, the processed sample may be delivered from the reagent channel 176 to the optical measurement channel 182 at a location upstream relative to the hydrodynamic focusing region 190. Sheath fluid may be introduced into the cartridge via a sheath fluid introduction port 198. The sheath fluid may be provided at such a flow rate that it surrounds the processed sample and forms a "sheath" around the sample "core". In some cases, the sheath fluid flow rate may be controlled such that it is higher than the processed sample flow rate to aid in core formation downstream within the hydrodynamic focusing region 190.

In some cases, as shown in the example shown in FIG. 3, the sheath fluid introduction port 198 may be fluidly coupled to a bifurcated sheath fluid delivery channel 202 including a first elongated sheath fluid sub channel 208 and a second elongated sheath fluid sub channel 212, but this is not required. The processed sample may be introduced into the first elongated sheath fluid channel 208 from the side at an intersecting region 216. In some cases, as shown, the processed sample may be introduced into first elongated sheath fluid sub channel at an angle, α, of approximately 90 degrees, relative to the direction of flow of the sheath fluid. It is contemplated that the processed sample may be introduced into first elongated sheath fluid sub channel at an angle, α, of between 5 and 175 degrees, between 25 and 115 degrees, between 45 and 135 degrees, between 60 and 150 degrees, between 85 and 95 degrees, or any other suitable angle relative to the direction of flow of the sheath fluid. This can be the case where only a single sheath fluid delivery channel is provided (not shown in FIG. 3), or a bifurcated sheath fluid delivery channel 202 is provided (as shown in FIG. 3).

When provided, the second elongated sheath fluid sub channel 212 may intersect with the first elongated sheath fluid sub channel 208 at a second intersection region 218 located downstream from the first intersection region 216. In some cases, and as shown in FIG. 3, the second elongated sheath fluid sub channel 212 may deliver a portion of the sheath fluid from a position located above the first sheath fluid sub channel 208 such that the sheath fluid from the second sheath fluid sub channel 212 enters the first sheath fluid sub channel 208 from the top. In some cases, the second elongated sheath fluid sub channel 212 may deliver another portion of the sheath fluid from a position located below the first sheath fluid sub channel 208 such that the sheath fluid from the second sheath fluid sub channel 212 enters the first sheath fluid sub channel 208 from the bottom. The combination of the processed sample entering the first sheath fluid sub channel 208 from the side coupled with the delivery of a portion of the sheath fluid from an upper position and/or lower position may facilitate better positioning of the core within the hydrodynamic focusing region. In some cases, this configuration may provide three-dimensional hydrodynamic focusing of the processed sample within the sheath fluid, which may result in a more reliable and accurate measurement of sample properties in the optical light scattering measurement channel 182. In the example shown, the sheath fluid carries the processed sample into the hydrodynamic focusing region 190 for hydrodynamic focusing of the processed sample and analysis by flow cytometry. The processed sample then passes from the optical scattering measurement channel 192 into a waste channel 222 where it is carried to a waste storage reservoir 226. In some cases, the waste storage reservoir 226 may be a self-contained, on-card waste storage reservoir.

In some cases, and as discussed above, the cartridge 150 may include an optical absorbance measurement region 162 including an optical absorbance measurement channel 230. In some cases, as least a portion of the optical absorbance measurement region 162 including the optical absorbance measurement channel 230 may pass over and/or under the optical light scattering measurement region 156, including the optical scattering measurement channel 192, but this is not required. According to an illustrative embodiment, the optical absorbance measurement channel 230 may include at least one sub channel "232" having a cuvette "234", including a transparent window "236". In some cases, as shown, the optical absorbance measurement channel 230 may include multiple sub channels 232a, 232b, and 232c, each of the sub channels 232a, 232b, and 232c having a corresponding cuvette 234a, 234b and 234c including a transparent window 236a, 236b, 236c, respectively, as shown. The number of sub channels "232" may be limited only by the amount of available space on the cartridge 150. For example, in some cases, the number of sub channels "232" may range from two to five sub channels "232". Providing an optical absorbance measurement channel 230 having multiple sub channels "232", each sub channel "232" having a cuvette "234" including a transparent window "236" through which light may pass for the optical absorbance measurement may facilitate simultaneous measurement of, for example, the concentration of multiple analytes of interest in a blood sample.

In some cases, as shown, the optical absorbance measurement channel 230 may include at least one gas permeable membrane 238 located downstream from of the one or more cuvettes 234a, 234b, and 234c. A vacuum port 240 may be located downstream from the gas permeable membrane 238 such that the gas permeable membrane 238 is positioned between the vacuum port 240 and the cuvettes 234a, 234b, and 234c. In some cases, each of the sub channels 232a, 232b, and 232c may include a gas permeable membrane associated with each of the sub channels 232a, 232b, and 232c, where the gas permeable membrane is located downstream from each of the cuvettes 234a, 234b, and 234c. In some embodiments, each of the sub channels 232a, 232b, and 232c may be in fluid communication with different vacuum ports located downstream from the gas permeable membranes, each of the different vacuum ports may be associated with one of the sub channels 232a, 232b, 232c, respectively. In other embodiments, at least some of the sub channels 232a, 232b, and 232c may be in fluid communication with a common vacuum port located downstream from the corresponding gas permeable membranes.

As shown in the illustrative embodiment provided by FIG. 3, the optical absorbance measurement channel 230 may include an on-card plasma separation region 242 to separate out the plasma portion of the fluid sample, and deliver the plasma portion of the fluid sample to one or more of the cuvettes 234a, 234b, and 234c. An exemplary on-card plasma separation region is shown and described in U.S. Provisional Application No. 61/446,924, filed on Feb. 25, 2011 entitled "SEPARATION, QUANTIFICATION AND CONTINUOUS PREPARATION OF PLASMA FOR USE IN A COLORIMETRIC ASSAY IN MICROFLUIDIC FORMAT," which is incorporated by reference herein in its entirety for all purposes. In the illustrative embodiment, the on-card plasma separation region 242 includes a plasma separation membrane or filter 243. In some cases, the flow of blood into and out of the plasma separation membrane 243 occurs in a transverse direction. As such, the membrane 243 may be positioned above the optical absorbance measurement channel 230, and a negative pressure may be applied from underneath the membrane 243 to pull the blood through the membrane 243 and plasma into each of the sub channels 232a, 232b, and 232c.

In the illustrative cartridge of FIG. 3, fluid sample may be introduced into the second sample loading channel 174 via the second sample introduction port 158. In some cases, the fluid sample may be a whole blood sample, but this is not required. The fluid sample may be then pulled through the sample loading channel 174 and into the optical absorbance measurement channel 230 by the application of a negative pressure to the vacuum port 240 provided in the cartridge 150. In some cases, the fluid sample may also be pulled through the on-card plasma separation region 242, before being accumulated in each of the cuvettes 234a, 234b, 234c for measurement using optical absorbance techniques. The sample may be pulled through the measurement channel 230 until the each of the sub channels 232a, 232b, 232c, including the cuvettes 234a, 234b, and 234c, are filled or substantially filled, and the fluid sample contacts the gas permeable membrane 238. The fluid sample may not pass through the at least one gas permeable membrane 238.

Figure 4:
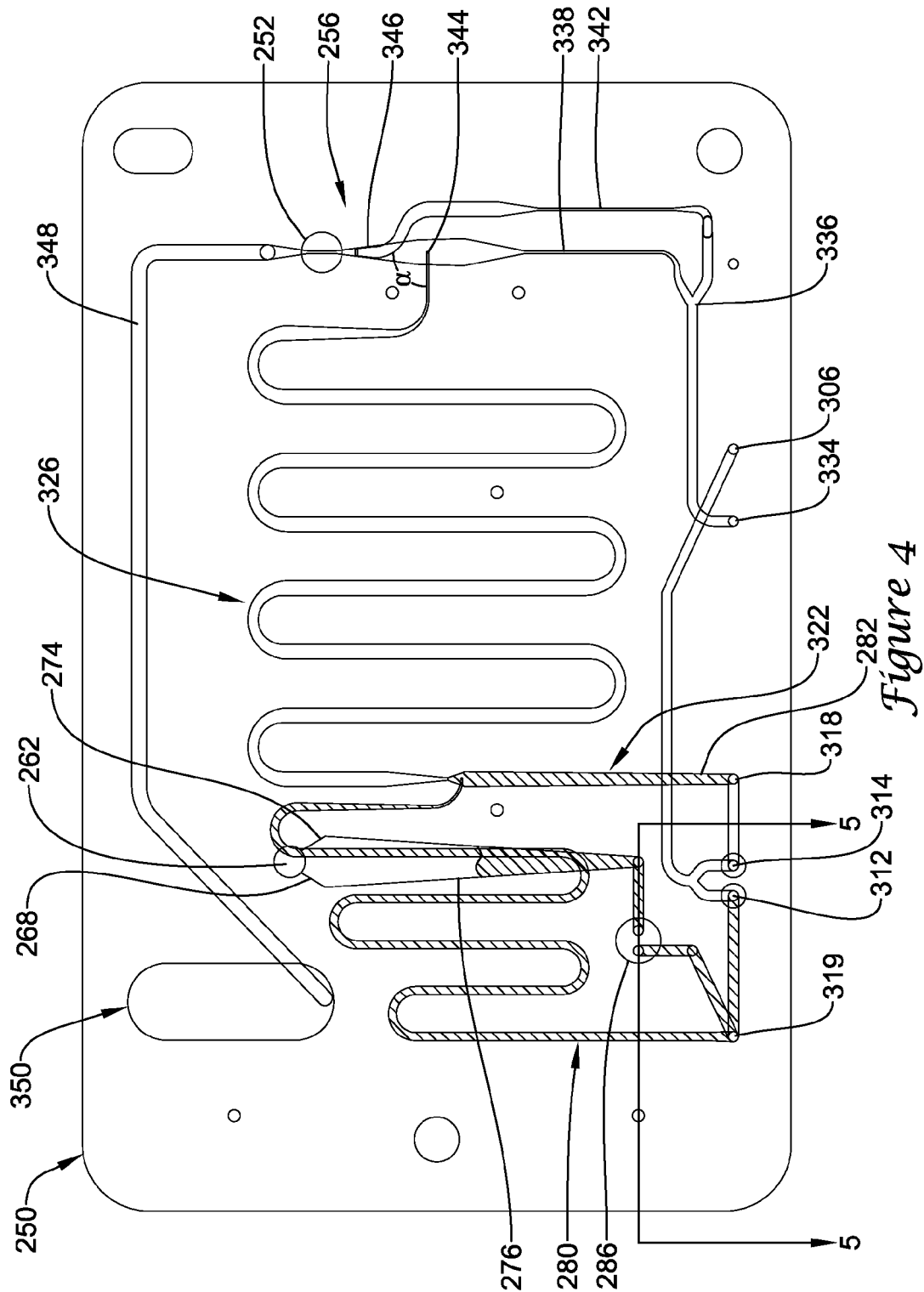
FIG. 4 is a front schematic view of an illustrative fluid analysis cartridge that may be received by a sample analyzer, such as the sample analyzer of FIG. 1.

FIG. 4 is a front schematic view of an illustrative fluid analysis cartridge 250 that may be received by a sample analyzer, such as the sample analyzer 12 of FIG. 1. In some embodiments, the cartridge 250 may be a disposable blood analysis cartridge configured to receive and retain a blood sample therein for analysis. As shown in FIG. 4, the cartridge 250 may be configured for optical light scattering measurements, and may include a hydrodynamic focusing region 256 and at least one optical light scattering measurement channel 252. At least one optical absorbance measurement channel, such as discussed above, may also be incorporated into the cartridge 250 depending upon the desired application, but this is not required.

As illustrated, cartridge 250 may include a sample introduction port 262 for receiving a fluid sample. In some cases, the fluid sample may be a whole blood sample. In some cases, the fluid sample may be obtained via a finger stick or blood draw. In the case in which the fluid sample is obtained via a finger stick, the blood may be collected by the cartridge directly from the patient's finger. In the case where the fluid sample is collected by a blood draw, sample may be obtained from the sample collection tube used to collect the fluid sample, and may be injected via a syringe or the like into the cartridge 250 via the sample introduction port 262. These are just some examples.

The sample introduction port 262 may be fluidly coupled to a sample collection reservoir 268 configured to receive and retain the fluid sample introduced through the sample introduction port 262. The sample collection reservoir 268 has a reservoir volume that is defined by its inner surfaces 274, and may have converging inner sidewalls 276 as shown in the illustrative embodiment. In some cases, the reservoir volume may be greater than a sample volume required for analysis. Sample may be drawn from the sample introduction port 262 into the sample collection reservoir 268 via capillary action. In some cases, the inner surfaces 274 of the sample collection reservoir 268 may be hydrophilic, and may in some cases include a hydrophilic surface treatment or coating disposed over at least a part of the inner surfaces 274 to facilitate capillary action. An anti-coagulant coating or surface treatment may also be disposed over at least a part of the inner surfaces 274 of the sample collection reservoir 268 in addition to or as an alternative to the hydrophilic surface treatment or coating, but this is not required. The converging inner sidewalls 276, which may converge in a direction away from the sample collection reservoir 268, may also help draw the fluid sample into the sample collection reservoir 268.

As shown in the illustrative example of FIG. 4, the cartridge 250 may include a sample loading channel 280 positioned downstream from and in fluid communication with the sample collection reservoir 268. In some cases, the cartridge 250 may include a valve 286 disposed between the sample collection reservoir 268 and the sample loading channel 280. In some cases, the cartridge may include one or more additional sample loading channels (not shown) in fluid communication with the sample collection reservoir. In such an instance, the valve 286 also may be disposed between the sample collection reservoir 268 and the one or more additional sample loading channels such that the valve 286 is common to both the sample loading channel 280 and any additional sample loading channels incorporated into the cartridge 250.

The valve 286 may include an inlet port (not visible) in fluid communication with the sample collection reservoir 268 and an outlet port (not visible) in fluid communication with the sample loading channel 280. The valve 286 may be configured to transition between an open state in which the sample collection reservoir 268 is placed in fluid communication with the sample loading channel 280, and a closed state in which the sample collection reservoir 268 is not in fluid communication with the sample loading channel 280. When in the closed state, the valve may prevent back flow of sample contained within the sample loading channel 280 back into the sample collection reservoir and out the sample introduction port 262. In some cases, the valve 286 may be actuated between its open and closed state by an actuator provided on the sample analyzer (e.g. sample analyzer 12) for this purpose, as will be described in greater detail below.

Figure 5A:
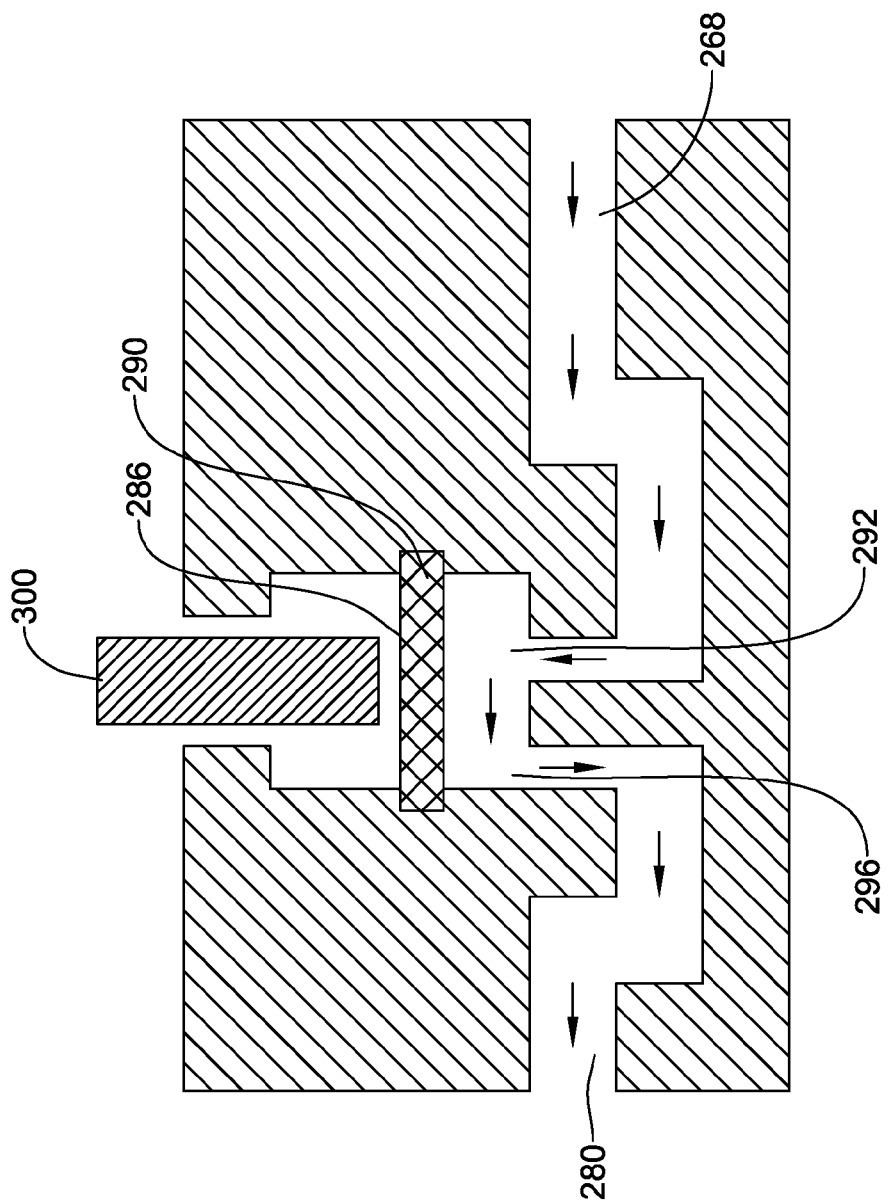
FIGS. 5A and 5B are partial side cross-sectional views of the illustrative cartridge shown in FIG. 4, taken along line 5-5.
Figure 5B:
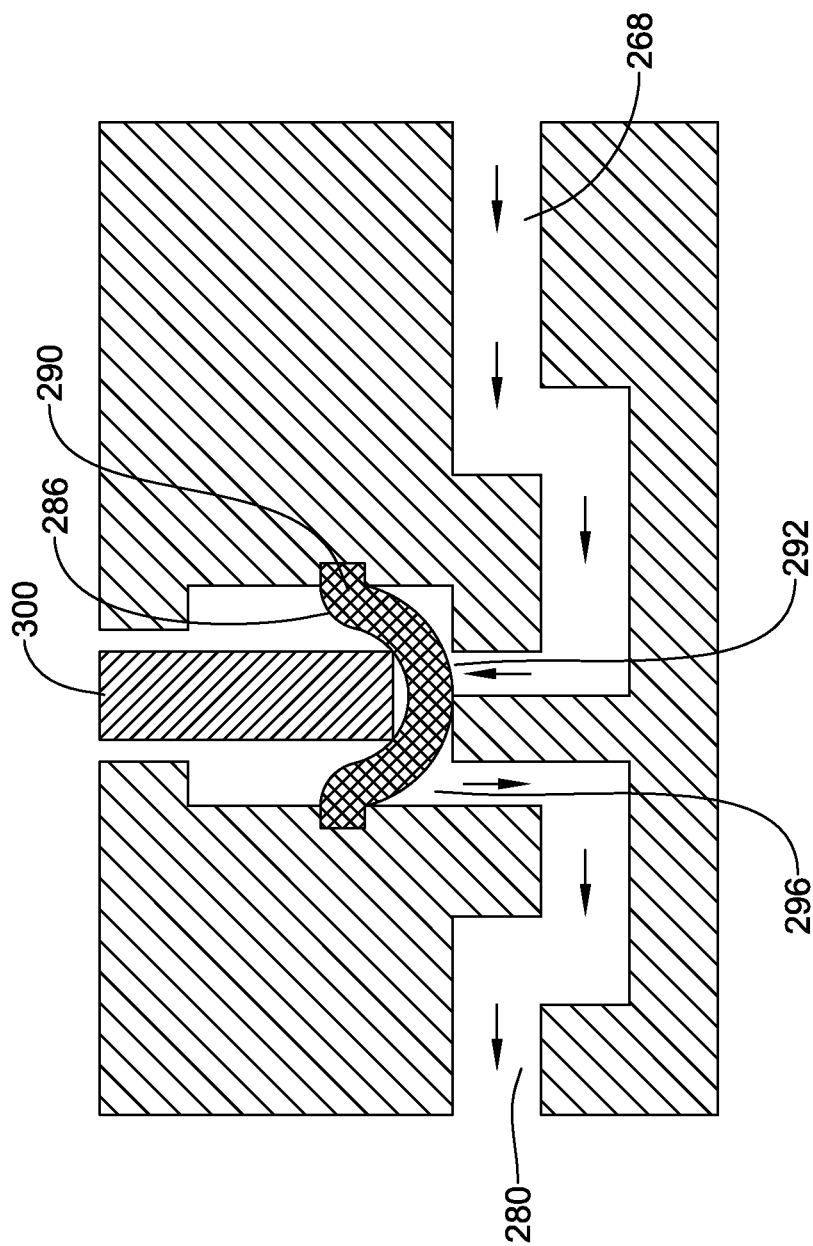

FIGS. 5A and 5B are partial side cross-sectional views of the illustrative cartridge shown in FIG. 4, taken along line 5-5. FIGS. 5A and 5B are not to scale. FIG. 5A depicts an illustrative valve 286 in an open state, and FIG. 5B depicts the illustrative valve 286 in a closed state. The valve shown in FIGS. 5A and 5B may be considered a pinch valve. As shown, the valve 286 may include a flexible portion 290 formed in a separate layer of the multi-layer cartridge 250, and may include a flexible material or membrane. The flexible portion 290 may be configured to flex between the open state (FIG. 5A) and the closed state (FIG. 5B) when pressure is applied. It is contemplated that the flexible portion 290 may have a variety of shapes and/or configurations such that in the open state the flexible portion 290 facilitates fluid flow between the sample collection reservoir 268 and the sample loading channel 280, and in the closed state the flexible portion 290 prevents or substantially prevents (less than 10% flow, less than 5% flow, less than 1% flow, relative to a fully open valve) flow between the sample collection reservoir 268 and the sample loading channel 280. In some cases, in the closed state, the flexible portion 290 prevents or substantially prevents less than about 1% fluid flow relative to a fully open valve.

The valve 286 may include an inlet port 292 and an outlet port 296. As shown in FIG. 5A, when in the open state, the fluid sample may flow from the sample collection reservoir 268, through the inlet port 292 of the valve 286, and then from the valve 286 into the sample loading channel 280 via the outlet port 296 of the valve 286. In some embodiments, such as shown in FIG. 5B, the actuator 300 located on the sample analyzer (e.g. sample analyzer 12) may be configured to contact and apply a downward pressure to the flexible portion 290 of the valve 286, causing the valve to depress, transitioning the valve 286 from the open state (FIG. 5A) to the closed state (FIG. 5B). The actuator 300 may be a plunger as shown, or may merely be an applied pressure (e.g. air pressure). As shown in FIG. 5B, in the closed state, the flexible portion 290 may block the inlet port 292 and/or the outlet port 296 to prevent fluid flow between the sample collection reservoir 268 and the sample loading channel 280.

Referring back to FIG. 4, cartridge 250 may include at least one vacuum port 306, and at least one gas permeable membrane 312 situated between the vacuum port 306 and the sample loading channel 280. In some embodiments, sample may be initially drawn into the sample collection reservoir 268 via capillary action, as discussed above, and then pulled from the sample collection reservoir 268 through the valve 286 (in the open state) and into the sample loading channel 280 by application of a negative pressure to the cartridge 250 via the vacuum port 306. In some cases, a negative pressure may be applied to the cartridge 250 until the sample loading channel 280 is filled and sample contacts the gas permeable membrane 312, indicating a complete fill. In some embodiments, negative pressure may be applied to the cartridge until the sample loading channel 280 and a lower portion 282 of a reagent channel 322 is also filled and contacts the gas permeable membrane 314. The valve 286 may then be actuated from the open position (FIG. 5A) to the closed position (FIG. 5B), as discussed above, to help prevent a backflow of fluid sample from the sample loading channel 280 into the sample collection reservoir 268. It will be understood that because the sample collection reservoir 268 may be configured to collect a greater sample volume than may be needed for analysis, a portion of the collected sample may remain in the sample collection reservoir 268 after the fluid sample has been pulled into the sample loading channel 280, but this is not required. As such, in some cases, a second pinch valve or other sealing element may be provided to seal the sample collection reservoir 268, but this is not required.

With the valve 286 closed, a pusher fluid may be introduced into the sample loading channel 280 via a pusher fluid introduction port 319 to move the fluid sample from the sample loading channel 280 to another region of the cartridge 250 for analysis. For example, as shown in FIG. 4, the fluid sample may be moved or pushed from the sample loading channel 280 into a reagent channel 322 including a mixing region 326. In the reagent channel 322, the fluid sample may be contacted with one or more reagents (e.g. lysing agent, sphering agent, diluent, etc.) introduced into the reagent channel via a reagent introduction port 318 where it may be processed for analysis. It will be understood that the number and/or type of reagents to be introduced into the reagent channel 322 may depend upon the application. The processed fluid sample may be then delivered from the mixing region 326 to the optical light scattering measurement channel 252 including a hydrodynamic focusing region 256 for analysis using, for example, flow cytometry.

The optical light scattering measurement channel 252 may be similar to that discussed above in reference to FIG. 3. The optical light scattering measurement channel 252 may include a sheath fluid introduction port 334 in fluid communication with, for example, a bifurcated sheath fluid delivery channel 336 including a first elongated sheath fluid sub channel 338 and a second elongated sheath fluid sub channel 342. The processed sample may be introduced into the first elongated sheath fluid channel 338 from the side at an intersecting region 344. In some cases, as shown, the processed sample may be introduced into first elongated sheath fluid sub channel at an angle, α, of approximately 90 degrees, relative to the direction of flow of the sheath fluid. It is contemplated that the processed sample may be introduced into first elongated sheath fluid sub channel at an angle, α, of between 5 and 175 degrees, between 25 and 115 degrees, between 45 and 135 degrees, between 60 and 150 degrees, between 85 and 95 degrees, or any other suitable angle relative to the direction of flow of the sheath fluid. This can be the case where only a single sheath fluid delivery channel is provided (not shown in FIG. 4), or a bifurcated sheath fluid delivery channel 336 is provided (as shown in FIG. 4).

When provided, the second elongated sheath fluid sub channel 342 may intersect with the first elongated sheath fluid sub channel 338 at a second intersection region 346 located downstream from the first intersection region 344. In some cases, as shown, the second elongated sheath fluid sub channel 342 may deliver a portion of the sheath fluid from a position located above the first sheath fluid sub channel 338 such that the sheath fluid from the second sheath fluid sub channel 342 enters the first sheath fluid sub channel 338 from the top. In some cases, the second elongated sheath fluid sub channel 342 may deliver another portion of the sheath fluid from a position located below the first sheath fluid sub channel 338 such that the sheath fluid from the second sheath fluid sub channel 342 enters the first sheath fluid sub channel 338 from the bottom. The combination of the processed sample entering the first sheath fluid sub channel 338 from the side coupled with the delivery of a portion of the sheath fluid from an upper position and/or lower position may facilitate better positioning of the fluid sample core within the hydrodynamic focusing region. In some cases, this configuration may provide three-dimensional hydrodynamic focusing of the processed sample within the sheath fluid, which may result in more reliable and accurate measurement of the sample properties in the optical light scattering measurement channel 252. In the example shown, the sheath fluid carries the processed fluid sample into the hydrodynamic focusing region 256 for hydrodynamic focusing of the processed sample and analysis by flow cytometry. The processed fluid sample may then pass from the optical scattering measurement channel 252 into a waste channel 348 where it may be carried to a waste storage reservoir 350. In some embodiments, the waste storage reservoir 350 may be an on-card waste storage reservoir configured to collect and retain the waste fluid in the cartridge 250 until disposal of the cartridge in an appropriate waste receptacle.

Figure 6:
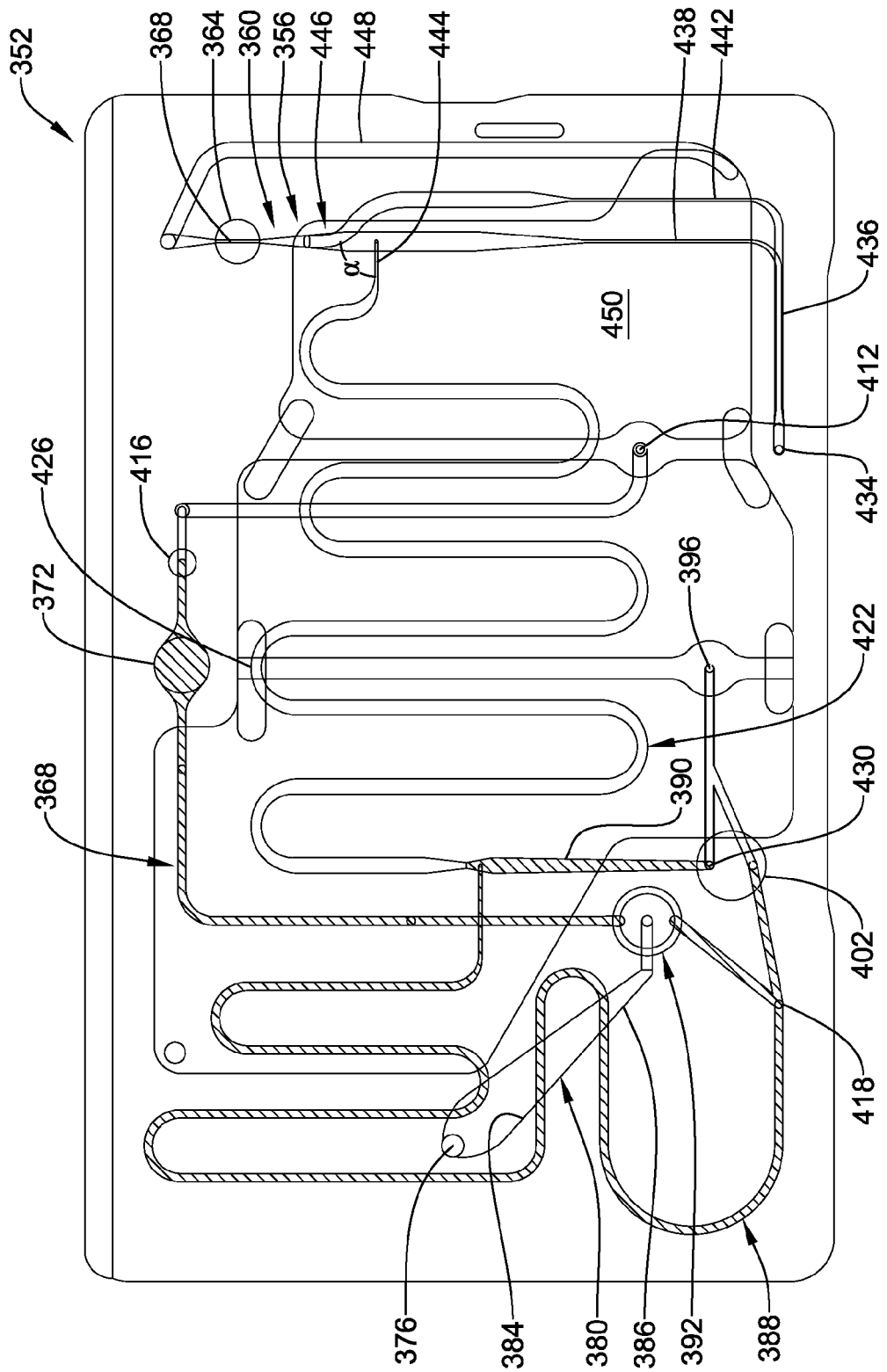
FIG. 6 is a front schematic view of an illustrative fluid analysis cartridge that may be received by a sample analyzer, such as the sample analyzer of FIG. 1.

FIG. 6 is a front schematic view of an illustrative fluid analysis cartridge 352 that may be received by a sample analyzer, such as the sample analyzer 12 of FIG. 1. In some embodiments, the cartridge 352 may be a disposable blood analysis cartridge configured to receive and retain a blood sample therein for analysis. As shown in FIG. 6, the cartridge 352 may be configured for optical light scattering measurements and optical absorbance measurements. For example, in FIG. 6, the cartridge 352 may include at least one optical light scattering measurement channel 356 having a hydrodynamic focusing region 360 disposed below a transparent window 364 for optical light scattering measurements, and an optical absorbance measurement channel 368 including at least one cuvette 372 for optical absorbance measurements. It will be understood that additional optical light scattering measurement channels and/or additional optical absorbance measurement channels may be incorporated into the cartridge 352 depending on the application. In some embodiments, the optical absorbance measurement channel 368 may include one or more sub channels, each sub channel having a cuvette as discussed above with reference to FIG. 3, but this is not required. Additionally, in some embodiments, the optical absorbance measurement channel 368 may include an on-card plasma separation region, as discussed above, through which the fluid sample may be passed to separate the plasma portion of the fluid sample such that the plasma portion of the fluid sample may be collected in the cuvette 372 for the optical absorbance measurement.

As illustrated, cartridge 352 may include a sample introduction port 376 for receiving a fluid sample. In some cases, the fluid sample may be a whole blood sample. The fluid sample may be obtained via a finger stick or blood draw. In the case in which the fluid sample is obtained via a finger stick, the blood may be collected by the cartridge 352 directly from the patient's finger. In the case where the fluid sample is collected by a blood draw, sample may be obtained from the sample collection tube used to collect the fluid sample, and may be injected via a syringe or the like into the cartridge 352 via the sample introduction port 376. These are just some examples.

The sample introduction port 376 may be fluidly coupled to a sample collection reservoir 380 configured to receive and retain the fluid sample introduced through the sample introduction port 376. The sample collection reservoir 380 has a reservoir volume that is defined by its inner surfaces 384, and may have converging inner sidewalls 386 as shown in the illustrative example. In some cases, the reservoir volume may be greater than a sample volume required for analysis. Sample may be drawn from the sample introduction port 376 into the sample collection reservoir 380 via capillary action. In some cases, the inner surfaces 384 of the sample collection reservoir 380 may be hydrophilic, and in some cases, may include a hydrophilic surface treatment or coating disposed over at least a part of the inner surfaces 384 to facilitate capillary action. An anti-coagulant coating or surface treatment may also be disposed over at least a part of the inner surfaces 384 of the sample collection reservoir 380 in addition to or as an alternative to the hydrophilic surface treatment or coating, but this is not required. The converging inner sidewalls 386, which may converge in a direction away from the sample collection reservoir 376, may also help draw the fluid sample into the sample collection reservoir 380.

As shown in the illustrative example of FIG. 6, the cartridge 352 may include a sample loading channel 388 positioned downstream from and in fluid communication with the sample collection reservoir 380. In addition, the cartridge 352 may also include a valve 392 disposed between the sample collection reservoir 380 and the sample loading channel 388. In some embodiments, the valve 392 may also be disposed between the sample collection reservoir 380 and an optical absorbance measurement channel 368 as shown in FIG. 6, such that the valve 392 is common to both the sample loading channel 388 and the optical absorbance measurement channel 368. Additionally, in some cases, the cartridge 352 may include one or more additional sample loading channels (not shown) in fluid communication with the sample collection reservoir 380. In such an instance, the valve 392 also may be disposed between the sample collection reservoir 380 and the one or more additional sample loading channels such that the valve 392 is common to both the sample loading channel 388 and any additional sample loading channels incorporated into the cartridge 352.

The valve 392 may be similar to the valve 286 shown and described with reference to FIGS. 4 and 5A-5B, and may include the same or similar features. In the illustrative embodiment shown in FIG. 6, the valve 392 may include an inlet port in fluid communication with the sample collection reservoir 380, and an outlet port in fluid communication with the sample loading channel 388 and/or the absorbance measurement channel 368. The valve 392 may be configured to transition between an open state, in which the sample collection reservoir 380 is placed in fluid communication with the sample loading channel 380 and/or the absorbance measurement channel 368, and a closed state in which the sample collection reservoir 380 is not in fluid communication with the sample loading channel 388 and/or the absorbance measurement channel 368. When in the closed state, the valve 392 may prevent back flow of sample contained within the sample loading channel 388 and/or the absorbance measurement channel 368 from entering back into the sample collection reservoir 380. In some cases, the valve 392 may be actuated between its open and closed state by an actuator (e.g. plunger and/or pressure source) provided by the sample analyzer (e.g. sample analyzer 12) for this purpose, as discussed in greater detail above with reference to FIGS. 5A and 5B.

In some cases, as shown in FIG. 6, the cartridge 352 may include a first vacuum port 396, and first gas permeable membrane 402 situated between the first vacuum port 396 and the sample loading channel 388. In some cases, the cartridge 352 may also include a second vacuum port 412 in fluid communication with the optical absorbance measurement channel 368 and a second gas permeable membrane 416 situated downstream of the cuvette 372 between the cuvette 372 and the second vacuum port 412. In the illustrative embodiment of FIG. 6, the fluid sample may be initially drawn into the sample collection reservoir 380 via capillary action. A portion of the fluid sample may then be pulled from the sample collection reservoir 380 through the valve 392 and into the sample loading channel 388 by application of a negative pressure to the cartridge 352 via the first vacuum port 396. In some cases, the fluid sample may be pulled from the sample collection reservoir 380 such that it substantially fills the sample loading channel 388 and a lower portion 390 of a reagent channel 422, as shown in FIG. 6. In addition, a portion of the fluid sample may be pulled from the sample collection reservoir 380 through the valve 392 and into the absorbance measurement channel 368 by application of a negative pressure to the cartridge 352 via the second vacuum port 412. The negative pressure may be applied to the first and second vacuum ports 396 and 412 at the same time or at different times (e.g. in a sequential manner) to pull sample from the sample collection reservoir 380 into the sample loading channel 388 and/or the absorbance measurement channel 368, as desired.

In some cases, a negative pressure may be applied to the cartridge 352 until the sample loading channel 388 is filled and sample contacts the first gas permeable membrane 402, indicating a complete fill. Additionally, a negative pressure may be applied to the cartridge 352 until the absorbance measurement channel 368 including cuvette 372 is completely filled and the fluid sample contacts the second gas permeable membrane 416. The valve 392 may then be actuated from an open position to a closed position, as discussed above, to help prevent a backflow of fluid sample from the sample loading channel 388 and/or the absorbance measurement channel 368 back into the sample collection reservoir 380. It will be understood that because the sample collection reservoir 380 may be configured to collect a greater sample volume than may be needed for analysis, a portion of the collected sample may remain in the sample collection reservoir 380 after the fluid sample has been pulled into the sample loading channel 388. As such, in some cases, a second pinch valve or other sealing element may be provided to seal the sample collection reservoir 380, if desired.

Figure 7:
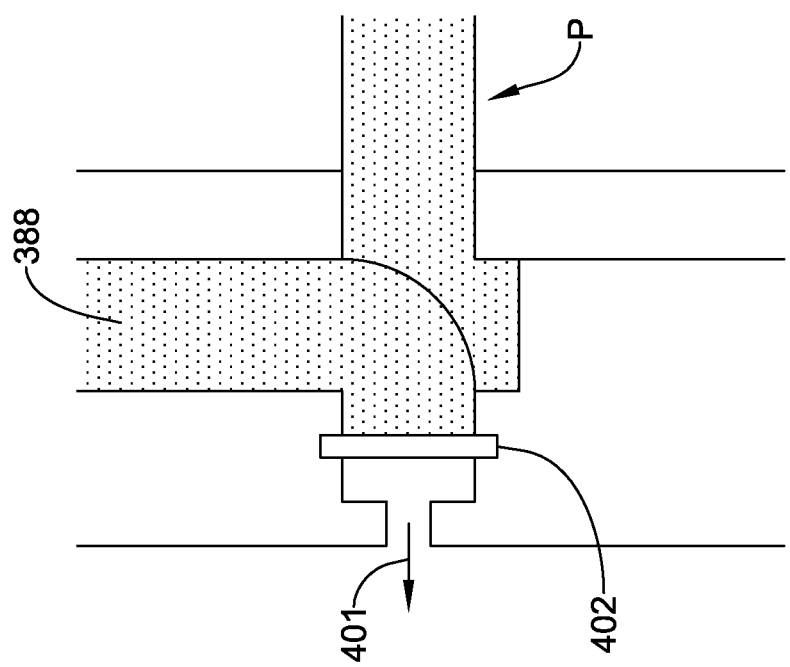
FIG. 7 is a partial cross-section view of a portion of the fluid analysis cartridge of FIG. 6.

FIG. 7 shows a partial, cross-section view a portion of the cartridge 352 including a gas permeable membrane such as, for example, first gas permeable membrane 402 disposed between the sample loading channel 388 and the first vacuum port 396. As shown in FIG. 7, application of a negative pressure 401 behind the gas permeable membrane 402 may be used to pull the fluid sample from the sample collection reservoir 380 (not visible in this figure) into the sample loading channel 388 until the fluid sample contacts the gas permeable membrane on the side opposite to negative pressure side. As discussed above, a pusher fluid P may be then introduced through the pusher fluid introduction port 418, and may be used to push the fluid sample from the sample loading channel 388 to another region of the cartridge 352 for analysis. The pusher fluid introduction port 418 may be sealed when the negative pressure 401 is applied behind the gas permeable membrane 402. Alternatively, the negative pressure 401 may be used to draw in pusher fluid P up to the gas permeable membrane 402, along with the fluid sample.

The ability to pull a fluid sample into the sample loading channel 388 up to the gas permeable membrane 402 may help reduce any air within the sample loading channel 388, and may help minimize any sample-air-pusher fluid interface. Additionally, the ability to pull a fluid sample into the sample loading channel 388 up to the gas permeable membrane 402 may minimize the presence of tiny air bubbles in the sample fluid, which may negatively impact the reliability and/or accuracy of the analysis performed by the cartridge.

Referring back to FIG. 6, a pusher fluid may be introduced into the sample loading channel 388 via a pusher fluid introduction port 418, which may move the fluid sample from the sample loading channel 388 to another region of the cartridge 352 for analysis. The fluid sample may be moved or pushed from the sample loading channel 388 into a reagent channel 422 including a mixing region 426. In the reagent channel 422, the fluid sample may be contacted with one or more reagents (e.g. lysing agent, sphering agent, diluent, etc.) introduced into the reagent channel 422 via a reagent introduction port 430 where it may be processed for analysis. It will be understood that the number and/or type of reagents to be introduced into the reagent channel 422 may depend upon the application. The processed fluid sample may be then delivered from the reagent channel 422 to the optical light scattering measurement channel 356 for analysis using, for example, flow cytometry.

The optical light scattering measurement channel 356 may be similar to that discussed above in reference to FIG. 3. The optical light scattering measurement channel 356 may include a sheath fluid introduction port 434 in fluid communication with a bifurcated sheath fluid delivery channel 436 including a first elongated sheath fluid sub channel 438 and a second elongated sheath fluid sub channel 442. The processed fluid sample may be introduced into the first elongated sheath fluid channel 438 from the side at an intersecting region 444. In some cases, as shown, the processed fluid sample may be introduced into first elongated sheath fluid sub channel 438 at an angle, $\alpha$, of for example approximately 90 degrees. Other angles are also contemplated. The second elongated sheath fluid sub channel 442 may intersect with the first elongated sheath fluid sub channel 438 at a second intersection region 446 located downstream from the first intersection region 444. In some cases, as shown, the second elongated sheath fluid sub channel 442 may deliver a portion of the sheath fluid from a position located above the first sheath fluid sub channel 438 such that the sheath fluid from the second sheath fluid sub channel 442 enters the first sheath fluid sub channel 438 from the top. In some cases, the second elongated sheath fluid sub channel 442 may deliver another portion of the sheath fluid from a position located below the first sheath fluid sub channel 438 such that the sheath fluid from the second sheath fluid sub channel 442 enters the first sheath fluid sub channel 438 from the bottom. The combination of the processed fluid sample entering the first sheath fluid sub channel 438 from the side coupled with the delivery of a portion of the sheath fluid from an upper position and/or lower position may facilitate better positioning of the fluid sample core within the hydrodynamic focusing region 360. In some cases, this configuration may provide three-dimensional hydrodynamic focusing of the processed sample within the sheath fluid, which may result in more reliable and/or accurate measurement of the sample properties in the optical light scattering measurement channel 356. In the example shown, the sheath fluid carries the processed sample into the hydrodynamic focusing region 364 for hydrodynamic focusing of the processed sample and analysis by flow cytometry. The processed fluid sample may then pass from the optical scattering measurement channel 356 into a waste channel 448 where it may be carried to a waste storage reservoir 450. In some embodiments, the waste storage reservoir 450 may be an on-card waste storage reservoir configured to collect and retain the waste fluid for disposal in an appropriate waste receptacle. An exemplary waste storage reservoir that may be incorporated into cartridge 352 will be described in greater detail below.

Figure 8:
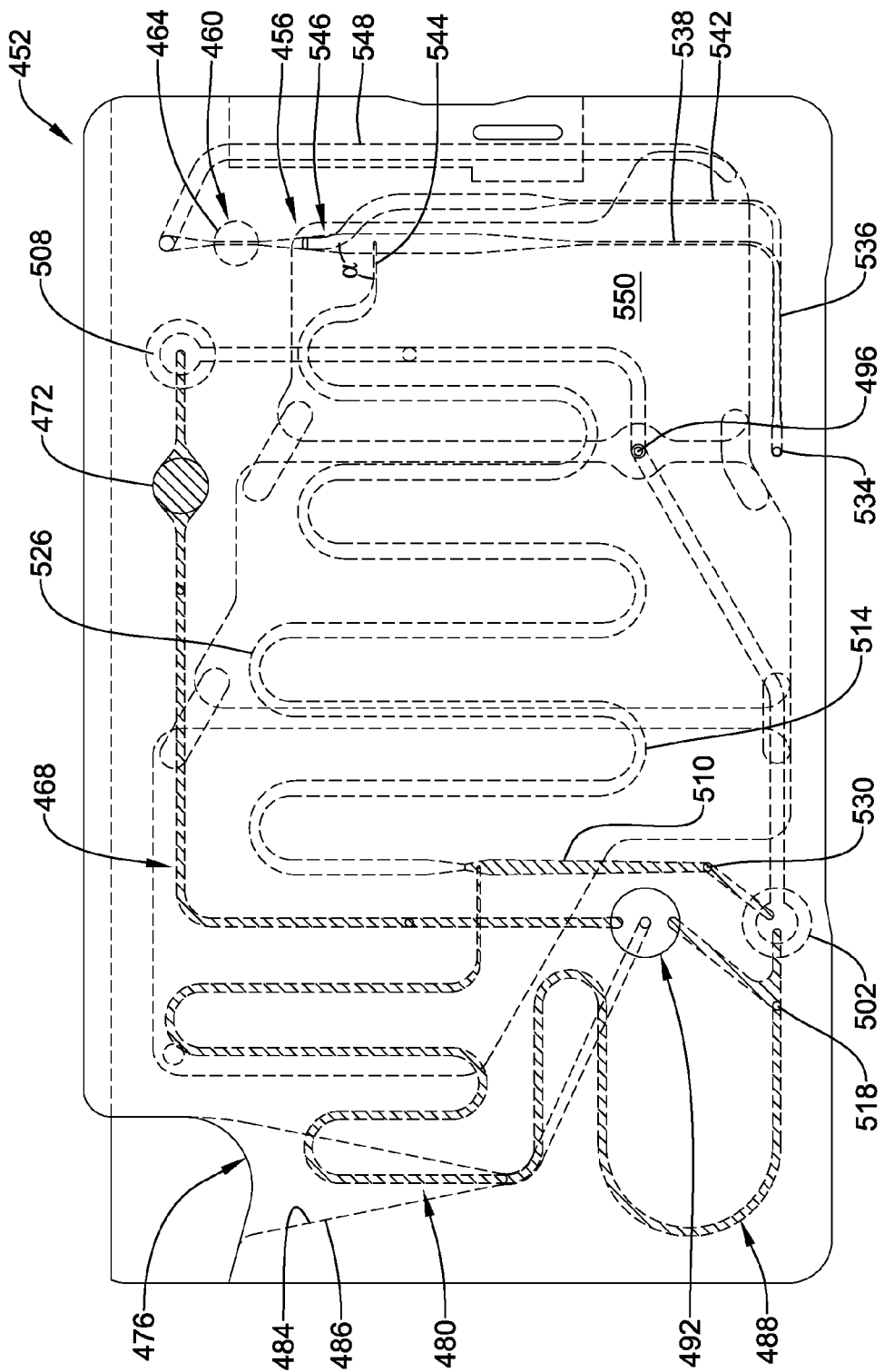
FIG. 8 is a front schematic view of an illustrative fluid analysis cartridge that may be received by a sample analyzer, such as the sample analyzer of FIG. 1.

FIG. 8 is a front schematic view of an illustrative fluid analysis cartridge 452 that may be received by a sample analyzer, such as the sample analyzer 12 of FIG. 1. In some embodiments, the cartridge 452 may be a disposable blood analysis cartridge configured to receive and retain a blood sample therein for analysis. As shown in FIG. 8, the cartridge 452 may be configured for optical light scattering measurements and optical absorbance measurements, but this is not required. For example, as shown, the cartridge 452 may include at least one optical light scattering measurement channel 456 having a hydrodynamic focusing channel 360 disposed below a transparent window 464 for optical light scattering measurements, and an optical absorbance measurement channel 468 including at least one cuvette 472 for optical absorbance measurements. It will be understood that additional optical light scattering measurement channels and/or additional optical absorbance measurement channels may be incorporated into the cartridge 452 depending upon the application. Additionally, in some embodiments, the optical absorbance measurement channel 468 may include one or more sub channels, each sub channel having a cuvette as discussed above in reference to FIG. 3, but this is not required.

As illustrated, cartridge 452 may include a sample introduction port 476 for receiving a fluid sample. In some cases, the fluid sample may be a whole blood sample. The fluid sample may be obtained via a finger stick or blood draw. In the case in which the fluid sample is obtained via a finger stick, the blood may be collected by the cartridge 452 directly from the patient's finger. In the case where the fluid sample is collected by a blood draw, the fluid sample may be obtained from the sample collection tube used to collect the fluid sample, and may be injected via a syringe or the like into the cartridge 452 via the sample introduction port 476. These are just some examples.

The sample introduction port 476 may be fluidly coupled to a sample collection reservoir 480 configured to receive and retain the fluid sample introduced through the sample introduction port 476. The sample collection reservoir 480 has a reservoir volume that is defined by its inner surfaces 484, and may have converging inner sidewalls 486 as shown in the illustrative example. In some cases, the reservoir volume may be greater than a sample volume required for analysis. Sample may be drawn from the sample introduction port 476 into the sample collection reservoir 480 via capillary action. In some cases, the inner surfaces 484 of the sample collection reservoir 480 may be hydrophilic, and may include a hydrophilic surface treatment or coating disposed over at least a part of the inner surfaces 484 to facilitate capillary action. An anti-coagulant coating or surface treatment may also be disposed over at least a part of the inner surfaces 484 of the sample collection reservoir 480 in addition to or as an alternative to the hydrophilic surface treatment or coating, but this is not required. The converging inner sidewalls 486, which may converge in a direction away from the sample collection reservoir 476, may also help draw the fluid sample into the sample collection reservoir 480.

As shown in FIG. 8, the cartridge 452 may include a sample loading channel 488 positioned downstream from and in fluid communication with the sample collection reservoir 480. In addition, the cartridge 452 may include a valve 492 disposed between the sample collection reservoir 480 and the sample loading channel 488. In some embodiments, the valve 492 may also be disposed between the sample collection reservoir 480 and an optical absorbance measurement channel 468 as shown in FIG. 8 such that the valve 492 is common to both the sample loading channel 488 and the optical absorbance measurement channel 468, but this is not required.

The valve 492 may be similar to the valve 286 shown and described with reference to FIGS. 4 and 5A-5B, and may include the same or similar features. In the illustrative embodiment of FIG. 8, the valve 492 may include an inlet port in fluid communication with the sample collection reservoir 480 and an outlet port in fluid communication with the sample loading channel 488 and the absorbance measurement channel 468. The valve 492 may be configured to transition between an open state in which the sample collection reservoir 480 is placed in fluid communication with the sample loading channel 488 and the absorbance measurement channel 468, and a closed state in which the sample collection reservoir 480 is not in fluid communication with the sample loading channel 488 and the absorbance measurement channel 468. When in the closed state, the valve 492 may help prevent back flow of sample contained within the sample loading channel 488 and/or the absorbance measurement channel 368 into the sample collection reservoir 488. In some cases, the valve 492 may be actuated between its open and closed state by an actuator provided by the sample analyzer (e.g. sample analyzer 12) for this purpose, as discussed in greater detail above with reference to FIGS. 5A and 5B.

In some cases, and as shown in FIG. 8, the cartridge 452 may include a vacuum port 496 and first gas permeable membrane 502 situated between the vacuum port 496 and the sample loading channel 488. Additionally, the cartridge 452 may also include a second gas permeable membrane 508 situated between the vacuum port 496 and the absorbance measurement channel 468, such that the vacuum port 496 is in fluid communication with both the sample loading channel 488 and the absorbance measurement channel 468. As shown in FIG. 8, the second gas permeable membrane 508 is located downstream of the cuvette 472, and between the cuvette 472 and the vacuum port 496. In the illustrative embodiment, the vacuum port 496 is common to both the sample loading channel 488 and the absorbance measurement channel 468, but this is not required. For example, separate vacuum ports may be provided, if desired.

The fluid sample may be initially drawn into the sample collection reservoir 480 via capillary action, as discussed above, and then a portion of the fluid sample may pulled from the sample collection reservoir 480 through the valve 492 and into the sample loading channel 388 by application of a negative pressure to the cartridge 452 via common vacuum port 496 until the fluid sample reaches the gas permeable membrane 502. In some cases, the negative pressure may be applied to the cartridge 452 until a portion of the fluid sample is pulled through the sample loading channel 488 and into a lower region 510 of a reagent channel 514 until it again reaches the gas permeable membrane 502. Pulling a portion of the fluid sample through the sample loading channel 488 and into a lower region 510 of the reagent channel 514 may facilitate an improved liquid-liquid interface between the fluid sample and a reagent introduced into the reagent channel 514.

In some cases, a portion of the fluid sample may also be pulled from the sample collection reservoir 480 through the valve 492 and into the absorbance measurement channel 468 by application of a negative pressure to the cartridge 452 via the same vacuum port 496. The negative pressure may be applied to the cartridge 452 to pull the fluid sample into the absorbance measurement channel 468 until the fluid sample fills or substantially fills the cuvette 472 and comes into contact with the second gas permeable membrane 508. The valve 492 may then be actuated from an open position to a closed position, as discussed above, to help prevent a backflow of fluid sample from the sample loading channel 488 and/or the absorbance measurement channel 468 back into the sample collection reservoir 480.

With the valve 492 closed, a pusher fluid may be introduced into the sample loading channel 488 via a pusher fluid introduction port 518 to move the fluid sample from the sample loading channel 588 to another region of the cartridge 552 for analysis. By pulling the fluid sample into the sample loading channel 488 such that it fills the entire sample loading channel 488 including the generally V-shaped region up to the gas permeable membrane 502 and across the pusher fluid introduction port 518, the presence of air bubbles may be reduced or eliminated and the fluid sample-pusher fluid interface may be improved. The reduction and elimination of air bubbles in the fluid sample and the improved fluid sample-pusher fluid interface may positively impact the reliability and/or accuracy of the analysis to be performed.

The fluid sample may be moved or pushed from the sample loading channel 488 into the reagent channel 514 including a mixing region 526. In the reagent channel 514, the fluid sample may be contacted with one or more reagents (e.g. lysing agent, sphering agent, diluent, etc.) introduced into the reagent channel 514 via a reagent introduction port 530 where it may be processed for analysis. It will be understood that the number and/or type of reagents to be introduced into the reagent channel 514 may depend upon the application. The processed fluid sample may be then delivered from the reagent channel 514 to the optical light scattering measurement channel 456 for analysis using, for example, flow cytometry.

The optical light scattering measurement channel 456 may be similar to that discussed above in reference to FIGS. 3, 4, and 6, discussed above. The optical light scattering measurement channel 456 may include a sheath fluid introduction port 534 in fluid communication with a bifurcated sheath fluid delivery channel 536 including a first elongated sheath fluid sub channel 538 and a second elongated sheath fluid sub channel 542. While a bifurcated sheath fluid delivery channel 536 is shown in FIG. 8, it is contemplated that a single sheath fluid delivery channel may be used, if desired. In FIG. 8, the processed fluid sample may be introduced into the first elongated sheath fluid sub channel 538 from the side at an intersecting region 544. In some cases, as shown, the processed fluid sample may be introduced into first elongated sheath fluid sub channel 538 at an angle, α, of approximately 90 degrees relative to the direction of flow of the sheath fluid. It is contemplated that the processed sample may be introduced into first elongated sheath fluid sub channel 538 at an angle, α, of between 5 and 175 degrees, between 25 and 115 degrees, between 45 and 135 degrees, between 60 and 150 degrees, between 85 and 95 degrees, or any other suitable angle relative to the direction of flow of the sheath fluid. This can be the case where only a single sheath fluid delivery channel is provided (not shown in FIG. 8), or a bifurcated sheath fluid delivery channel 536 is provided (as shown in FIG. 8).

The second elongated sheath fluid sub channel 542 may intersect with the first elongated sheath fluid sub channel 538 at a second intersection region 546 located downstream from the first intersection region 544. In some cases, as shown, the second elongated sheath fluid sub channel 542 may deliver a portion of the sheath fluid from a position located above the first sheath fluid sub channel 538 such that the sheath fluid from the second sheath fluid sub channel 542 enters the first sheath fluid sub channel 538 from the top. In some cases, the second elongated sheath fluid sub channel 546 may deliver another portion of the sheath fluid from a position located below the first sheath fluid sub channel 538 such that the sheath fluid from the second sheath fluid sub channel 546 enters the first sheath fluid sub channel 538 from the bottom. The combination of the processed fluid sample entering the first sheath fluid sub channel 538 from the side coupled with the delivery of a portion of the sheath fluid from an upper position and/or lower position may facilitate better positioning of the fluid sample core within the hydrodynamic focusing region 460 of the optical light scattering measurement channel 456. In some cases, this configuration may provide three-dimensional hydrodynamic focusing of the processed sample within the sheath fluid, which may result in more reliable and accurate measurement of the sample properties. In the example shown, the sheath fluid carries the processed sample into the hydrodynamic focusing region 460 for hydrodynamic focusing of the processed sample and analysis by flow cytometry. The processed fluid sample may then pass from the optical scattering measurement channel 456 into a waste channel 548 where it may be carried to a waste storage reservoir 550. In some embodiments, the waste storage reservoir 550 may be an on-card waste storage reservoir configured to collect and retain the waste fluid for disposal in an appropriate waste receptacle. An exemplary waste storage reservoir that may be incorporated into cartridge 552 will be described in greater detail below.

Figure 9:
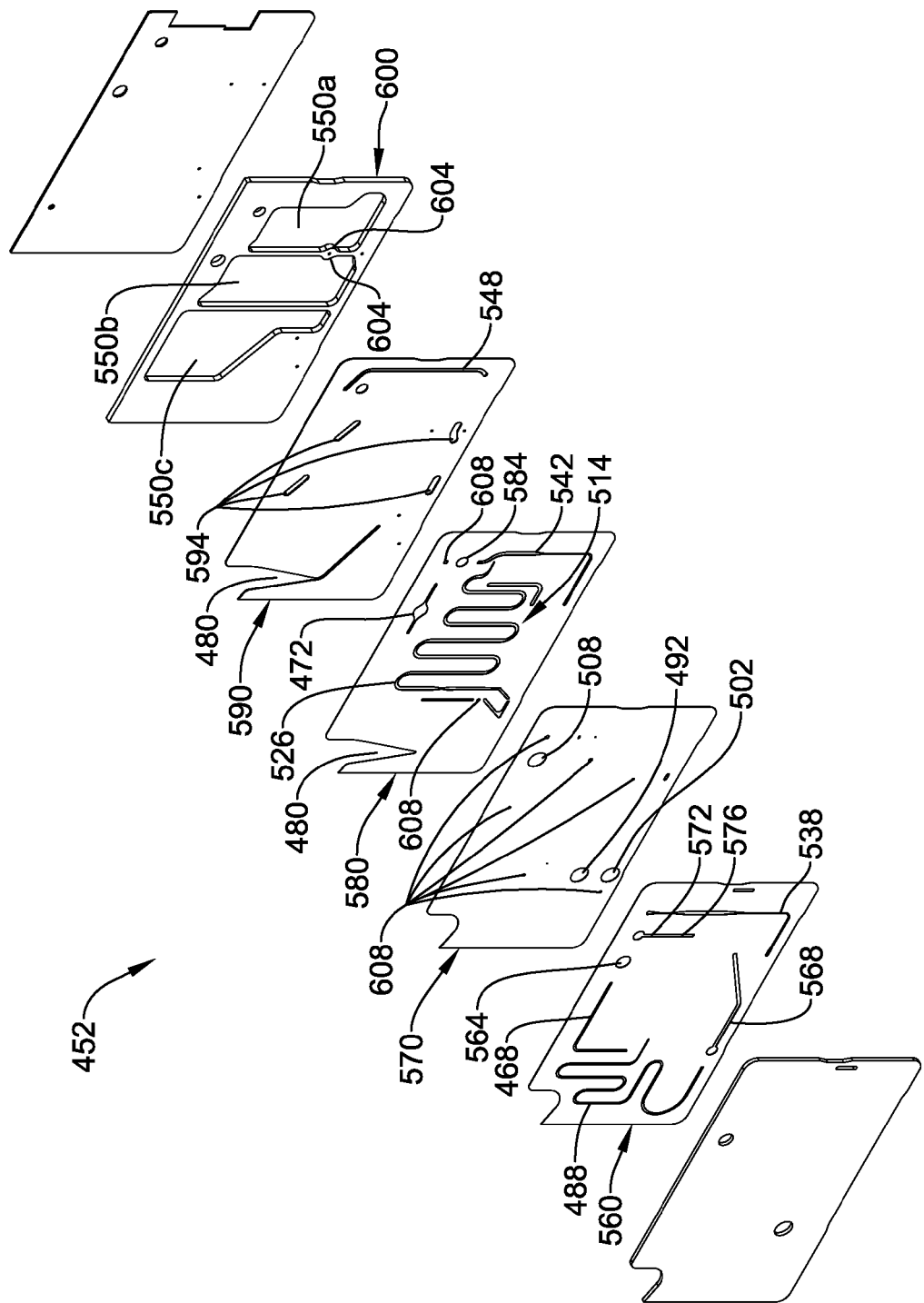
FIG. 9 is an exploded view of the illustrative fluid analysis cartridge of FIG. 8.

FIG. 9 is an exploded view of the exemplary cartridge 452 shown in FIG. 8. As shown in FIG. 9, the cartridge 452 may be a multi-layered cartridge including multiple layers. In some cases, as shown, the cartridge 452 may include up to seven layers. Additional or fewer layers may be incorporated into the cartridge 452 depending upon the desired application and type of sample to be analyzed.

As shown in FIG. 9, portions of the various channels incorporated into the cartridge 452 (e.g. optical light scattering measurement channel 456, optical absorbance measurement channel 468, sample loading channel 488 and reagent channel 514) may be formed in different layers of a multi-layered cartridge 452. In some cases, this may facilitate at least a portion of a first channel to pass over and/or under at least a portion of a second channel, as discussed above. For example, in some embodiments, at least a portion of the optical absorbance measurement channel 468 may pass over and/or under at least a portion of the optical light scattering measurement channel 456 and/or the reagent channel 514. The ability to layer different portions of different channels may facilitate the inclusion of multiple channels for different purposes within the cartridge. Additionally, the ability to form different channels in different layers may facilitate a better usage of the available space on the cartridge 452, which may facilitate an overall reduction in the size of the cartridge 452.

For example, in some cases, a portion of the optical absorbance measurement channel 468, the sample loading channel 488, and the first elongated sheath fluid sub channel 538 of the optical light absorbance measurement channel 468 may be formed in a first layer 560 of the multi-layered cartridge 352. In some cases, as shown, the first layer 560 may also include at least one transparent window 564 for facilitating the optical absorbance measurement of the fluid sample, and a first vacuum line 568 and a portion 572 of a second vacuum line 576 for applying a negative pressure to the cartridge 452 as described above.

In some embodiments, the valve 492 and the gas permeable membranes 502 and 508 may be provided in a separate layer 570 that may be disposed between the first layer 560, as discussed above, and an additional layer 580 that may include the reagent channel 514, the cuvette 472 of the optical absorbance measurement channel 468 which may be disposed under the transparent window 564 provided in the first layer 560, the second elongated sheath fluid sub channel 542, and a second transparent measurement window 584 that may facilitate the optical light scattering measurement. Yet another layer 590 may include the sample collection reservoir 480 and the waste channel 548. Additionally, layer 590 may also include one or more pass-throughs 594 for passage of waste fluid some one region of the waste storage reservoir 550 to the next.

In some embodiments, as shown in FIG. 9, the waste storage reservoir 550 may be formed in a separate layer 600 of the multi-layered cartridge 452. In some cases, the waste storage reservoir 550 may include multiple segments 550a, 550b, and 550c. The pass-throughs 594, discussed above, may facilitate transfer of waste from a first segment (e.g. segment 550a) to another segment (e.g. 550b) of the waste storage reservoir 550. In some embodiments, the waste storage reservoir 550 may include one or more ribs 604 that extend upwards away from a bottom of the layer 600 and which may provide additional structural integrity to the cartridge 452.

Various vias 608 formed in different layers of the cartridge 452 may facilitate transfer of the liquid sample between the different layers of the cartridge 452 as the fluid sample is moved from one region of the card to another for analysis. In some cases, the location and placement of the vias 608 may facilitate the reduction and/or elimination of tiny air bubbles in the fluid sample. Additionally, one or more vias 608 provided in the cartridge 452 may facilitate the escape of air from the cartridge 452 when a negative pressure is applied such that a more complete evacuation of any air present within the cartridge may 452 be achieved.

Figure 10:
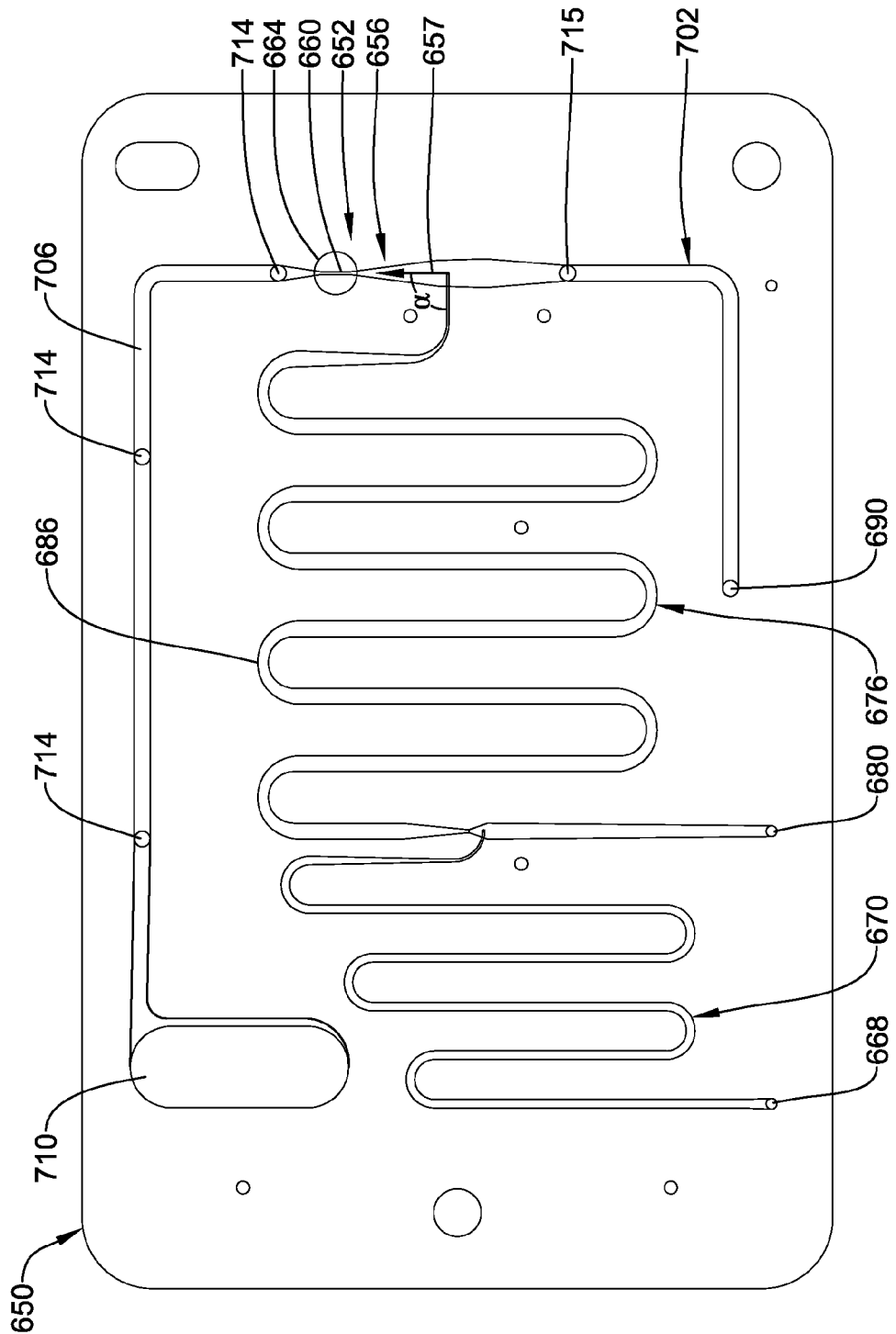
FIG. 10 is front schematic view of an illustrative fluid analysis cartridge that may be received by a sample analyzer, such as the sample analyzer of FIG. 1.

FIG. 10 is a front schematic view of an illustrative fluid analysis cartridge 650 that may be received by a sample analyzer, such as the sample analyzer 12 of FIG. 1. In some embodiments, the cartridge 650 may be a disposable blood analysis cartridge configured to receive and retain a blood sample therein for analysis. As shown in FIG. 10, the cartridge 650 may include at least one optical light scattering measurement channel 656 having a hydrodynamic focusing channel 660 disposed adjacent a transparent window 664 for optical light scattering measurements. Although not shown, in some cases the cartridge 650 may also include an optical absorbance measurement channel, such as describe detail above. It will be understood that additional optical light scattering measurement channels and/or additional optical absorbance measurement channels may be incorporated into the cartridge 650, depending upon the desired application.

In some cases, and as shown in FIG. 10, the cartridge 650 may include at least one sample introduction port 668 for introduction of a sample into the cartridge 650. In some cases, the sample introduction port 668 may include an anti-coagulant coating provided on an inner surface thereof to facilitate sample loading. In other cases, the sample introduction port 668 may include a hydrophilic coating which may facilitate loading of the sample via capillary action. However, this is not required. In some cases, the sample introduction port may be configured to mate with and/or receive a syringe for delivery of a fluid sample into the cartridge 650, but again, this is not required. Any suitable fluid connection for delivery of a fluid sample into the cartridge 650 may be used.

As illustrated in the example of FIG. 10, the sample introduction port 668 may be in fluid communication with a sample loading channel 670, a reagent channel 676, and the optical light scattering measurement channel 656. Once a sample is loaded into the sample loading channel 670, a pusher fluid may be introduced via the sample introduction port 668 (or some other port) to push the sample from the sample loading channel 670 into the reagent channel 676, which in the illustrative embodiment. In some cases, the reagent channel 676 may include a reagent introduction port 680 for introduction of one or more reagents into the reagent channel 676 for processing the sample. The number and/or type of reagents to be introduced into the reagent channel 676 may depend upon the application. For example, the reagents may include a lysing reagent, a sphering reagent, a diluent, etc. The reagent introduced through the reagent introduction port 680 may contact and mix with the sample entering the reagent channel 676 from the sample loading channel 670. In some embodiments, the reagent channel 676 may include a number of bends or turns 686 that may help increase the length of the reagent channel 676, which may increase the length of time the sample spends in the reagent channel. In some cases, as shown, the bend or turn 686 may be a substantially U-shaped bend or turn 686, and may help keep particles such as blood cells dispersed as the sample travels through the reagent channel 676. The increase in dwell or residence time may provide a sufficient amount of time needed for the reagent to properly react with and process the sample for analysis. The processed sample may then delivered from the reagent channel 676 to the optical light scattering measurement channel 656 for analysis using an optical light scattering measurement technique such as, for example, flow cytometry.

The optical scattering measurement channel 656 may include a hydrodynamic focusing channel 660 over which a transparent window 664 may be disposed. In some cases, the length of the hydrodynamic focusing channel may be reduced, such as from 2 mm to 1.5 mm, 1.0 mm, 0.5 mm or less. This may help reduce backpressure in the optical light scattering measurement channel 656 of the cartridge 650.

In the example shown, sheath fluid may be introduced into the cartridge via a sheath fluid introduction port 690. The sheath fluid may be provided at such a flow rate that it surrounds the processed sample and forms a "sheath" around the sample "core". In some cases, the sheath fluid flow rate may be controlled such that it is higher than the processed sample flow rate to aid in core formation downstream within the hydrodynamic focusing region 660. As shown in FIG. 10, the cartridge 650 may include a single sheath fluid channel 702, and may not include a second or bifurcated sheath fluid delivery channel, although this is not required. Utilizing a single sheath fluid channel 702 may help facilitate a reduction in the performance variation due to changes in flow balance that may be present when utilizing two sheath fluid delivery channels. A single sheath fluid delivery channel, coupled with a shorter hydrodynamic focusing channel may help facilitate stabilization of fluid sample flow within the cartridge 650, which may in some cases increase the overall accuracy and/or the reliability of the fluid analysis.

In some cases, the processed sample may be delivered from the reagent channel 676 to the optical measurement channel 656 at a location upstream relative to the hydrodynamic focusing channel 660. In some cases, as shown, the processed sample may be introduced from the reagent channel 676 into the sheath fluid channel 702 at an angle, $\alpha$, of approximately 90 degrees relative to the direction of flow 657 of the sheath fluid. It is contemplated that the processed sample may be introduced from the reagent channel 676 into the sheath fluid channel 702 at an angle, $\alpha$, of between 5 and 175 degrees, between 25 and 115 degrees, between 45 and 135 degrees, between 60 and 150 degrees, between 85 and 95 degrees, or any other suitable angle, relative to the direction of flow 657 of the sheath fluid. Delivery of the processed sample at such an angle may facilitate better positioning of the sample "core" within the hydrodynamic focusing channel 660.

In some cases, the reagent channel 676 may undergo a bend or otherwise change direction just upstream of the optical measurement channel 656. In some cases, such a bend or change in direction in the reagent channel 676 may cause the processed sample to rotate about 90 degrees just upstream of the optical measurement channel 656. In some cases, this may move the cell stream from the floor of the reagent channel 676 to the side wall. In some cases, this rotation may place the cells away from the ceiling and floor of the optical measurement channel 656 for better core formation. Once injected into the optical scattering measurement channel 656, the processed sample may be carried by the sheath fluid through the optical scattering measurement channel 656 and into a waste channel 706, where it is carried to a waste storage reservoir 710.

In some cases, the waste storage reservoir 710 may be a self-contained, on-card waste storage reservoir. In some cases, the waste channel 706 may commute between different layers of the laminated cartridge 650, which may increase the overall structural integrity of the cartridge 650 during manufacture. Additionally, the waste storage reservoir 710 may include a capillary groove on an inner surface thereof, which may help prevent waste fluid aggregation.

In some cases, the cartridge 650 may include one or more vias 714, sometimes having a reduced cross-section relative to the flow channels between which they are disposed. Such vias 714 may be located throughout the cartridge and may be disposed between two regions of a single channel and/or two different fluid channels on the cartridge. In some instances, for example, a via 714 having a reduced cross-sectional area relative to part of the waste channel 706 in one layer of the laminated cartridge 650 to another part of the waste channel 706 in another layer of the laminated cartridge 650. In another example, a via 715 having a reduced cross-sectional area relative to part of the sheath fluid channel 702 in one layer of the laminated cartridge 650 to another part of the sheath fluid channel 702 in another layer of the laminated cartridge 650. In some cases, this may help reduce the frequency of air bubbles in the sheath fluid channel 702 downstream of via 715.

The cartridges, as discussed herein according to the various embodiments may be formed by any of the techniques known in the art, including molding, machining, and etching. The various cartridges can be made of materials such as metal, silicon, plastics, and polymers, and combinations thereof. In some cases, the cartridges may be formed from a single sheet, from two sheets, or from a plurality of laminated sheets. The individual sheets forming the multi-layered cartridges of the present disclosure need not be formed from the same material. For example, different layers may have different rigidities such that a more rigid layer may be used to strengthen the overall structural integrity of the exemplary cartridges while a more flexible layer or portion of a layer may be used to form at least a portion of the valve structure as described herein. The various channels and flow regions of the cartridge may be formed in different layers and/or the same layer of an exemplary cartridge. The different channels and/or ports may be machined, die cut, laser ablated, etched, and/or molded. The different sheets forming the laminated structure may be bonded together using an adhesive or other bonding means.

Having thus described several illustrative embodiments of the present disclosure, those of skill in the art will readily appreciate that yet other embodiments may be made and used within the scope of the claims hereto attached. Numerous advantages of the disclosure covered by this document have been set forth in the foregoing description. It will be understood, however, that this disclosure is, in many respect, only illustrative. Changes may be made in details, particularly in matters of shape, size, and arrangement of parts without exceeding the scope of the disclosure. The disclosure's scope is, of course, defined in the language in which the appended claims are expressed.

What is claimed is:

1. A disposable cartridge for blood analysis comprising:
   a sample introduction port for receiving a fluid sample;
   a sample loading channel in fluid communication with the sample introduction port;
   a reagent channel in fluid communication with the sample loading channel, the reagent channel including a mixing region wherein the fluid sample is mixed with a reagent to produce a processed sample;
   a sheath channel in fluid communication with the reagent channel, the sheath channel for carrying a flow of a sheath fluid, wherein the reagent channel is configured to deliver the processed sample through a sidewall of the sheath channel and introduce the processed sample into the sheath channel at an angle of between 45 and 135 degrees relative to a direction of fluid flow of the sheath fluid within the sheath channel;
   a measurement channel including a hydrodynamic focusing region disposed adjacent a transparent window, wherein the processed sample is carried by the sheath fluid from the sheath channel into the measurement channel and past the transparent window; and
   an on-board waste storage reservoir in fluid communication with the measurement channel, the on-board waste storage reservoir configured to receive the processed sample and the sheath fluid after they have passed through the measurement channel.

2. The disposable cartridge of claim 1, wherein the cartridge does not include a bifurcated sheath channel.

3. The disposable cartridge of claim 1, further comprising a waste channel configured to carry the processed sample and the sheath fluid to the on-board waste storage reservoir, the waste channel entering the on-board waste storage reservoir in a top region of the on-board waste storage reservoir such that the processed sample and the sheath fluid enter the on-board waste storage reservoir from the top region and flow toward a bottom region of the on-board waste storage reservoir.

4. The disposable cartridge of claim 3, further comprising a via disposed between the measurement channel and the waste channel, the via having a reduced cross-sectional area relative to a cross-sectional area of the measurement channel.

5. The disposable cartridge of claim 1, wherein the reagent channel is configured to deliver the processed sample through the sidewall of the sheath channel and introduce the processed sample into the sheath channel at an angle of approximately 90 degrees relative to a direction of fluid flow of the sheath fluid within the sheath channel.

6. The disposable cartridge of claim 1, wherein the reagent channel is configured to deliver the processed sample through the sidewall of the sheath channel and introduce the processed sample into the sheath channel at an angle of between 85 and 95 degrees relative to a direction of fluid flow of the sheath fluid within the sheath channel.

7. The disposable cartridge of claim 1, further comprising an optical absorbance measurement channel.

8. The disposable cartridge of claim 1, wherein the sheath channel does not include a narrowed region upstream of the measurement channel.

9. The disposable cartridge of claim 1, wherein at least part of the sample introduction port is configured to mate with and receive at least part of a syringe for delivery of the fluid sample into the disposable cartridge.

* * * * *